(12) United States Patent
Ko et al.

(10) Patent No.: US 12,274,718 B2
(45) Date of Patent: Apr. 15, 2025

(54) COMPOSITION AND METHOD FOR PREVENTING, ALLEVIATING, OR TREATING LIVER INJURY

(71) Applicant: KoBioLabs, Inc., Seoul (KR)

(72) Inventors: Gwang Pyo Ko, Seoul (KR); Won Kim, Seoul (KR); Hyun Ju You, Incheon (KR); Giljae Lee, Seoul (KR); Bo-Ram Cho, Seoul (KR)

(73) Assignee: KOBIOLABS, INC., Seoul (KR)

( * ) Notice: Subject to any disclaimer, the term of this patent is extended or adjusted under 35 U.S.C. 154(b) by 521 days.

(21) Appl. No.: 17/626,628

(22) PCT Filed: Jul. 30, 2020

(86) PCT No.: PCT/KR2020/010097
§ 371 (c)(1),
(2) Date: Jan. 12, 2022

(87) PCT Pub. No.: WO2021/020923
PCT Pub. Date: Feb. 4, 2021

(65) Prior Publication Data
US 2022/0257669 A1    Aug. 18, 2022

(30) Foreign Application Priority Data

| Jul. 30, 2019 | (KR) | 10-2019-0092689 |
| Jul. 14, 2020 | (KR) | 10-2020-0087105 |
| Jul. 30, 2020 | (KR) | 10-2020-0094922 |
| Jul. 30, 2020 | (KR) | 10-2020-0095361 |

(51) Int. Cl.
| A61K 39/02 | (2006.01) |
| A23L 33/135 | (2016.01) |
| A61K 35/74 | (2015.01) |
| A61P 1/16 | (2006.01) |
| C12N 1/20 | (2006.01) |
| G01N 33/569 | (2006.01) |

(52) U.S. Cl.
CPC ............ *A61K 35/74* (2013.01); *A23L 33/135* (2016.08); *A61P 1/16* (2018.01); *C12N 1/20* (2013.01); *G01N 33/56916* (2013.01); *G01N 2333/26* (2013.01); *G01N 2333/36* (2013.01)

(58) Field of Classification Search
None
See application file for complete search history.

(56) References Cited

U.S. PATENT DOCUMENTS

| 2009/0291469 A1 | 11/2009 | David |
| 2012/0071451 A1 | 3/2012 | Spenard et al. |
| 2016/0143961 A1 | 5/2016 | Berry et al. |
| 2017/0290889 A1 | 10/2017 | Loke et al. |
| 2018/0273940 A1 | 9/2018 | Sommer et al. |
| 2019/0282638 A1 | 9/2019 | Sokol et al. |

FOREIGN PATENT DOCUMENTS

| CN | 102361642 | 2/2012 |
| CN | 108135944 | 6/2018 |
| CN | 108990420 | 12/2018 |
| JP | 2006-349457 | 12/2006 |
| JP | 2008-538893 | 11/2008 |
| JP | 6351328 | 7/2018 |
| JP | 2018112482 | 7/2018 |
| JP | 2019-517783 | 6/2019 |
| KR | 10-2012-0008034 | 1/2012 |
| KR | 10-2018-0010237 | 1/2018 |
| KR | 10-2019-0026687 | 3/2019 |
| KR | 10-2021-0014576 | 2/2021 |
| WO | 2010-106420 | 9/2010 |
| WO | 2016-086161 | 6/2016 |
| WO | 2016-086208 | 6/2016 |
| WO | 2017075098 | 5/2017 |
| WO | 2017120495 | 7/2017 |
| WO | 2018-064165 | 4/2018 |
| WO | 2018-065132 | 4/2018 |
| WO | 2018-118941 | 6/2018 |
| WO | 2018-156916 | 8/2018 |
| WO | 2019-032575 | 2/2019 |
| WO | 2019-118515 | 6/2019 |
| WO | 2022-236365 | 11/2022 |

OTHER PUBLICATIONS

Jerome Boursier et al., "The Severity of Nonalcoholic Fatty Liver Disease Is Associated With Gut Dysbiosis and Shift in the Metabolic Function of the Gut Microbiota", Hepatology, vol. 63, No. 3, pp. 764-775, Mar. 2016.
Rohit Loomba et al., "Gut Microbiome-Based Metagenomic Signature for Non-invasive Detection of Advanced Fibrosis in Human Nonalcoholic Fatty Liver Disease", Cell Metabolism 25, 1054-1062, May 2, 2017.
Jasmohan S. Bajaj et al., "Altered profile of human gut microbiome is associated with cirrhosis and its complications", Journal of Hepatology 2014 vol. 60:940-947, May 2014.
Nan Qin et al., "Alterations of the human gut microbiome in liver cirrhosis", Nature 2014; vol. 513:59-64, Sep. 2014.
Yan He et al., "Regional variation limits applications of healthy gut microbiome reference ranges and disease models", Nature Medicine vol. 24, 1532-1535, Oct. 2018.
Bo Kyung Koo et al., "Additive effects of PNPLA3 and TM6SF2 on the histological severity of non-alcoholic fatty liver disease", Journal of Gastroenterology and Hepatology 33 (2018) 1277-1285, Nov. 2017.

(Continued)

*Primary Examiner* — Jennifer E Graser
(74) *Attorney, Agent, or Firm* — LEX IP MEISTER, PLLC

(57) ABSTRACT

The present invention relates to a composition for preventing, alleviating or treating liver injury, for example, nonalcoholic fatty liver, and more specifically, it relates to a composition for preventing or treating liver injury comprising a *Ruminococcus* spp. strain.

14 Claims, 16 Drawing Sheets
Specification includes a Sequence Listing.

(56) References Cited

OTHER PUBLICATIONS

Elizabeth M. Brunt et al., "Nonalcoholic Steatohepatitis: A Proposal for Grading and Staging the Histological Lesions", The American Journal of Gastroenterology vol. 94, No. 9, 2467-2474, Sep. 1999.
Elizabeth M. Brunt et al., "Nonalcoholic Fatty Liver Disease (NAFLD) Activity Score and the Histopathologic Diagnosis in NAFLD: Distinct Clinicopathologic Meanings", Hepatology, vol. 53, No. 3:810-820, Mar. 2011.
David E. Kleiner et al., "Design and Validation of a Histological Scoring System for Nonalcoholic Fatty Liver Disease", Hepatology, vol. 41, No. 6, 1313-1321, Jun. 2005.
J Gregory Caporaso et al., "QIIME allows analysis of high-throughput community sequencing data", nature methods, vol. 7 No. 5, 335-336, May 2010.
Lawrence A. David et al., "Diet rapidly and reproducibly alters the human gut microbiome", Nature (2014)505.559-563, Jan. 2014.
Jari Oksanen et al., "The vegan Package", Community ecology package (2007)10, Oct. 3, 2007.
Xochitl C Morgan et al., "Dysfunction of the intestinal microbiome in inflammatory bowel disease and treatment", Genome Biology vol. 13, Article No. R79, Sep. 2012.
Junjie Qin et al., "A metagenome-wide association study of gut microbiota in type 2 diabetes", Nature vol. 490, pp. 55-60, Oct. 2012.
KIPO, A PCT Search Report & Written Opinion of PCT/KR2020/010097, dated Nov. 26, 2020.
Mingliang Jin et al., "Faecal microbiota from patients with cirrhosis has a low capacity to ferment non-digestible carbohydrates into short-chain fatty acids", Liver International. 2019;39:1437-1447, Aug. 2019.
Baohong Wang et al., "Altered Fecal Microbiota Correlates with Liver Biochemistry in Nonobese Patients with Non-alcoholic Fatty Liver Disease", Scientific Reports 6:32002, Aug. 2016.
S.M.B. Duarte et al., "Gut microbiome composition in lean patients with NASH is associated with liver damage independent of caloric intake: A prospective pilot study", Nutrition, Metabolism & Cardiovascular Diseases 28, 369-384, Oct. 2017.
Sebastião M.B. Duartea et al., "Microbiota and nonalcoholic fatty liver disease/nonalcoholic steatohepatitis (NAFLD/NASH)", Annals of Hepatology, vol. 18, pp. 416-421, Apr. 2019.
Kim, Min-Soo, et al. "*Ruminococcus faecis* sp. nov., isolated from human faeces." The Journal of Microbiology 49 (Jun. 30, 2011): 487-491.
Shiyu Wang, Chief editor, "Medicinal adjuvant science" China Medical Press. Beijing: China (Apr. 2019) pp. 89-90.
Xie, Yirui. "Characterization of intestinal microbial communities and effect of intestinal microbiota alteration on hepatic damage in rats with acute rejection after liver transplantation." Doctoral dissertation at College of Medicine of Zhejiang University (Mar. 1, 2012): pp. 1-100.
Canadian Intellectual Property Office, Office Action of the corresponding CA Patent Application No. 3,148,434 dated Feb. 14, 2023.
JPO, Office Action of the corresponding Japanese Patent Application No. 2022-505546 dated Mar. 28, 2023.
EPO, Search Report of EP 20848228.1 dated Jun. 6, 2023.
Reham M Abdou et al., "Gut Microbiota of Nonalcoholic Fatty Liver Disease," Digestive Diseases and Sciences, vol. 61, pp. 1268-1281, Feb. 2016, doi: https://doi.org/10.1007/s10620-016-4045-1.
Fabiana de Faria Ghetti et al., "Influence of gut microbiota on the development and progression of nonalcoholic steatohepatitis," European Journal of Nutrition, vol. 57, No. 3, pp. 861-876, Sep. 2017, doi: https://doi.org/10.1007/s00394-017-1524-x.
Zahra Safari et al., "The links between the gut microbiome and non-alcoholic fatty liver disease (NAFLD)," Cellular and Molecular Life Sciences, vol. 76, No. 8, pp. 1541-1558, Jan. 2019, doi: https://doi.org/10.1007/s00018-019-03011-w.
Stavros Bashiardes et al., "Non-alcoholic fatty liver and the gut microbiota," Molecular Metabolism, vol. 5, No. 9, pp. 782-794, Sep. 2016, doi: https://doi.org/10.1016/j.molmet.2016.06.003.
Christopher Leung et al., "The role of the gut microbiota in NAFLD," Nature Reviews Gastroenterology & Hepatology, vol. 13, No. 7, pp. 412-425, Jun. 2016, doi: https://doi.org/10.1038/nrgastro.2016.85.
E Grace et al., "Review article: small intestinal bacterial overgrowth—prevalence, clinical features, current and developing diagnostic tests, and treatment," Alimentary Pharmacology & Therapeutics, vol. 38, No. 7, pp. 674-688, Oct. 2013, doi: https://doi.org/10.1111/apt.12456.
A Wieland et al., "Systematic review: microbial dysbiosis and nonalcoholic fatty liver disease," Alimentary Pharmacology & Therapeutics, vol. 42, No. 9, pp. 1051-1063, Aug. 2015, doi: https://doi.org/10.1111/apt.13376.
Saumya Jayakumar et al., "Review article: emerging role of the gut microbiome in the progression of nonalcoholic fatty liver disease and potential therapeutic implications," Alimentary Pharmacology & Therapeutics, vol. 50, No. 2, pp. 144-158, May 2019, doi: https://doi.org/10.1111/apt.15314.
Aleksandra A Kolodziejczyk et al., "The role of the microbiome in NAFLD and NASH," EMBO Molecular Medicine, p. e9302, Dec. 2018, doi: https://doi.org/10.15252/emmm.201809302.
James B. Thissen et al., "Axiom Microbiome Array, the next generation microarray for high-throughput pathogen and microbiome analysis," PLOS ONE, vol. 14, No. 2, p. e0212045, Feb. 2019, doi: https://doi.org/10.1371/journal.pone.0212045.
Aharon Oren et al., "List of new names and new combinations previously effectively, but not validly, published", International journal of systematic and evolutionary microbiology. 2019. vol. 69. No. 1. p. 5-9, Jan. 2019.
SIPO, Notice of Allowance of the corresponding CN Patent Application No. 202080055877.4, dated Nov. 1, 2023.
Rospatent, Notice of Allowance of the corresponding RU Patent Application No. 2022102310, dated Dec. 1, 2023.
Min-Soo Kim et al., "*Ruminococcus faecis* sp. nov., isolated from human faeces", The Journal of Microbiology 49 (2011): 487-491, Jun. 30, 2011.
Mingliang Jin et al., "Faecal microbiota from patients with cirrhosis has a low capacity to ferment non-digestible carbohydrates into short-chain fatty acids." Liver International Liver International 39.8 (2019): 1437-1447, Apr. 2019.
JPO, Office Action of JP 2022-506047 dated Jan. 10, 2023.
IP Australia, Office Action of the corresponding AU Patent Application No. 2020320244., dated Mar. 13, 2024, total 6 pages.
Aragonès Gemma et al. "Gut microbiota-derived mediators as potential markers in nonalcoholic fatty liver disease." BioMed research international 2019, thesis No. 8507583, pp. 1-10 (Jan. 2, 2019).
Zhu, Lixin et al. "Characterization of gut microbiomes in nonalcoholic steatohepatitis (NASH) patients: a connection between endogenous alcohol and NASH." Hepatology 57.2 (Feb. 2013): 601-609.
T.S. Krolevets et al. "Clinical and laboratory markers for the prediction of liver fibrosis in persons with non-alcoholic fatty liver disease." Experimental and Clinical Gastroenterology. 2018 (7): 43-51, dissertation abstract only.
Rospatent, Office Action of RU 2022102171 dated Sep. 12, 2022.
Rospatent, Office Action of RU 2022102310 dated Sep. 12, 2022.

【FIG. 1a】
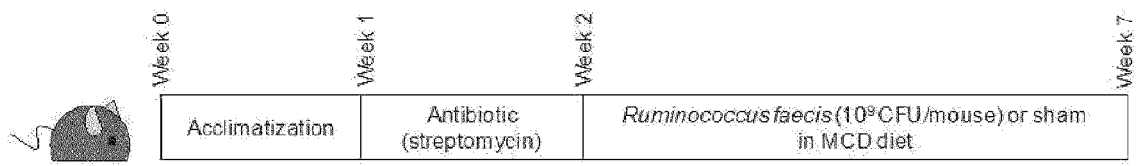
【FIG. 1b】
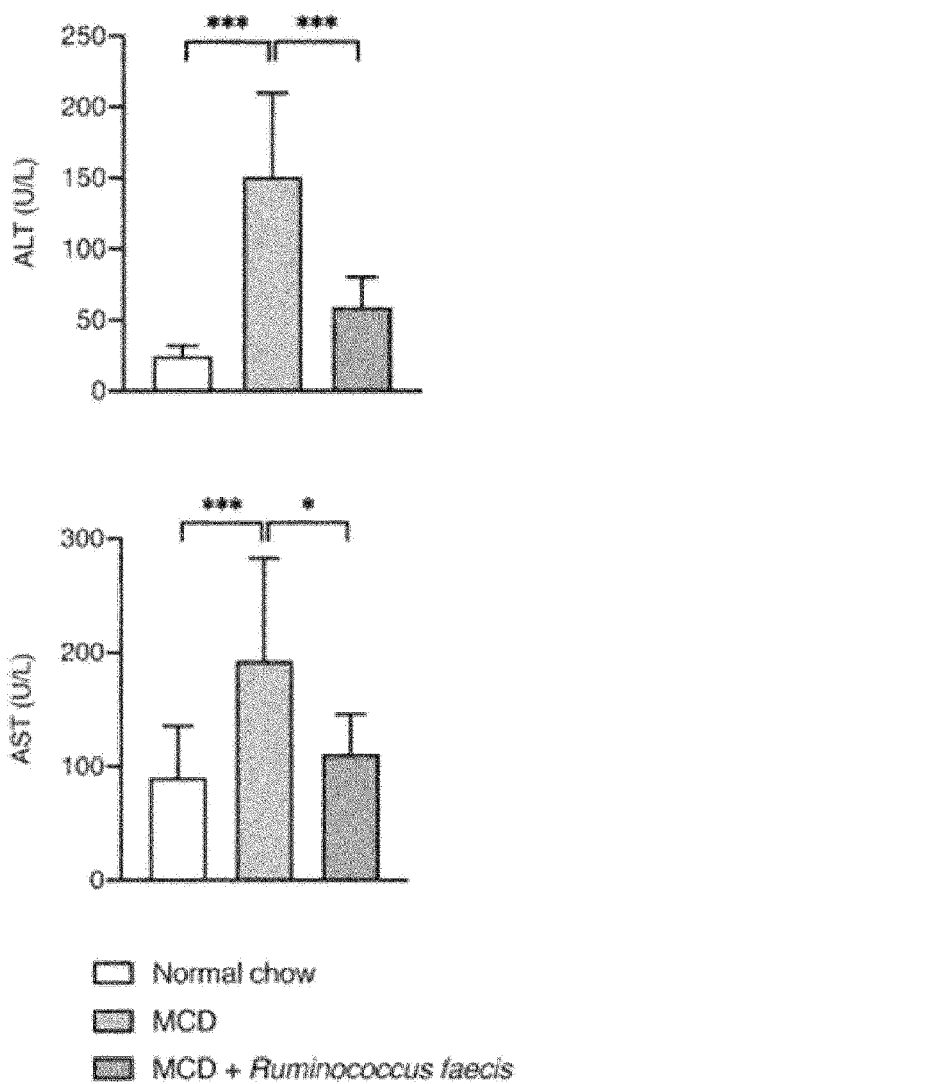

[FIG. 1c]
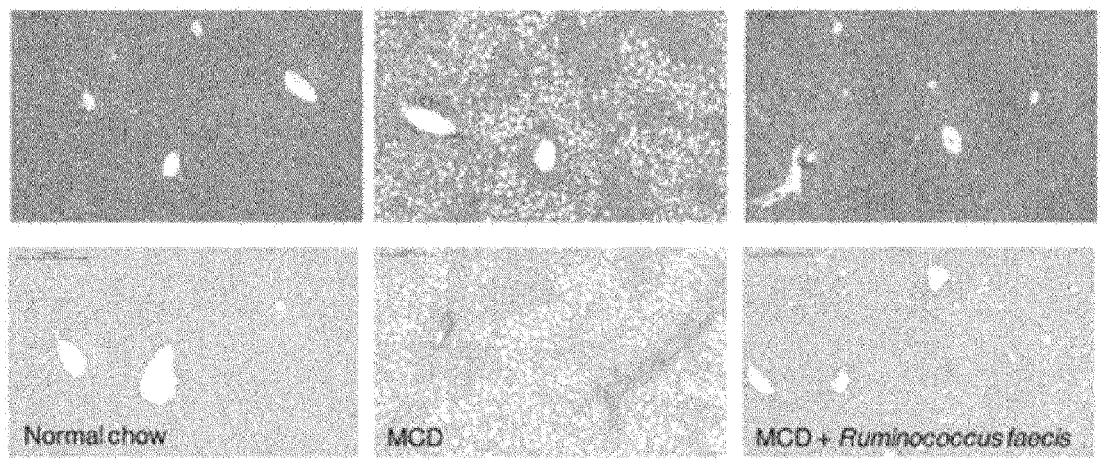

[FIG. 1d]
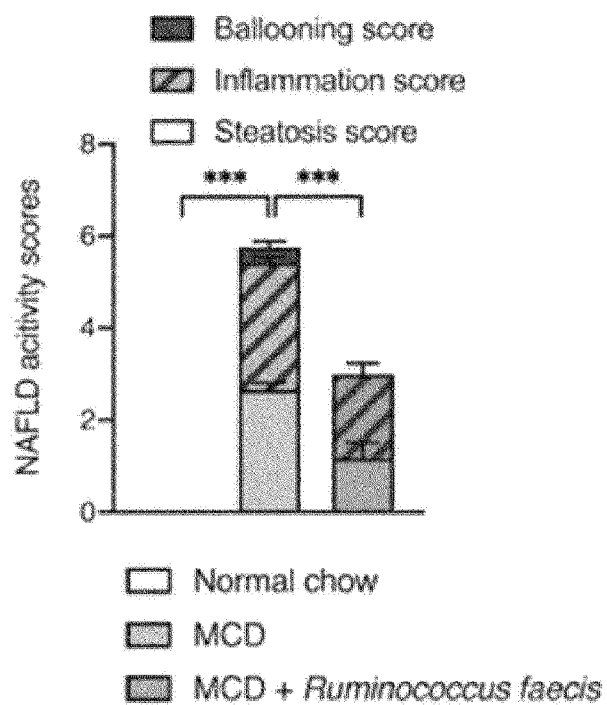

[FIG. 1e]
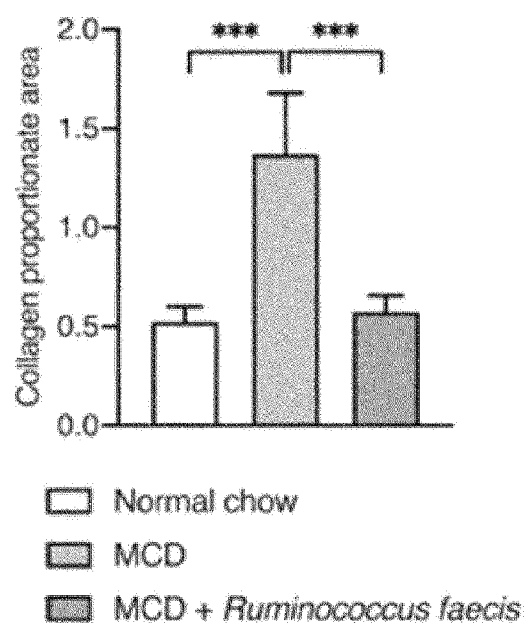

[FIG. 1f]
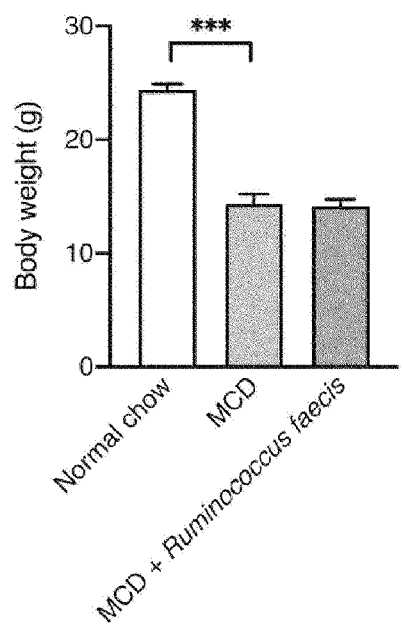

[FIG. 1g]
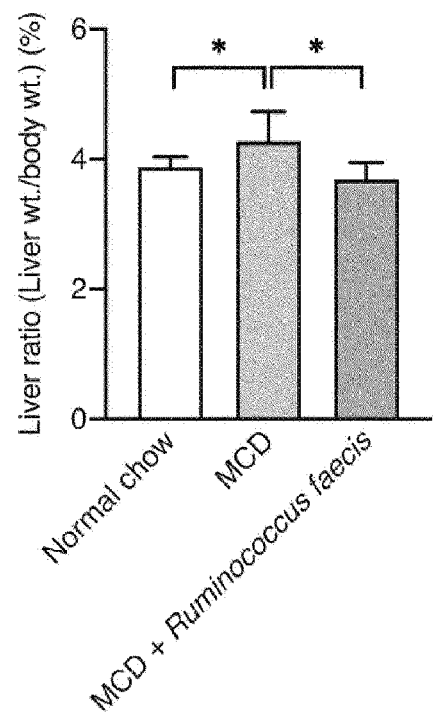

【FIG. 1h】
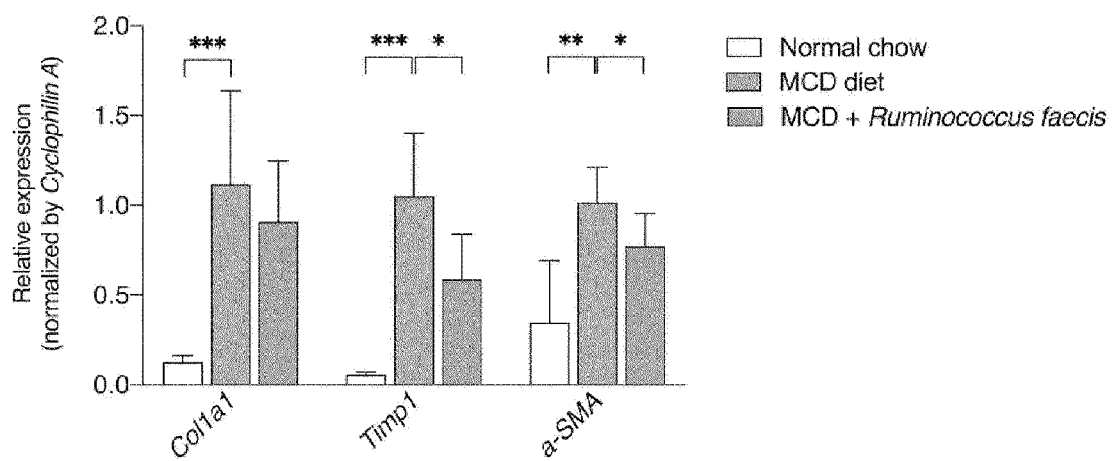
【FIG. 1i】
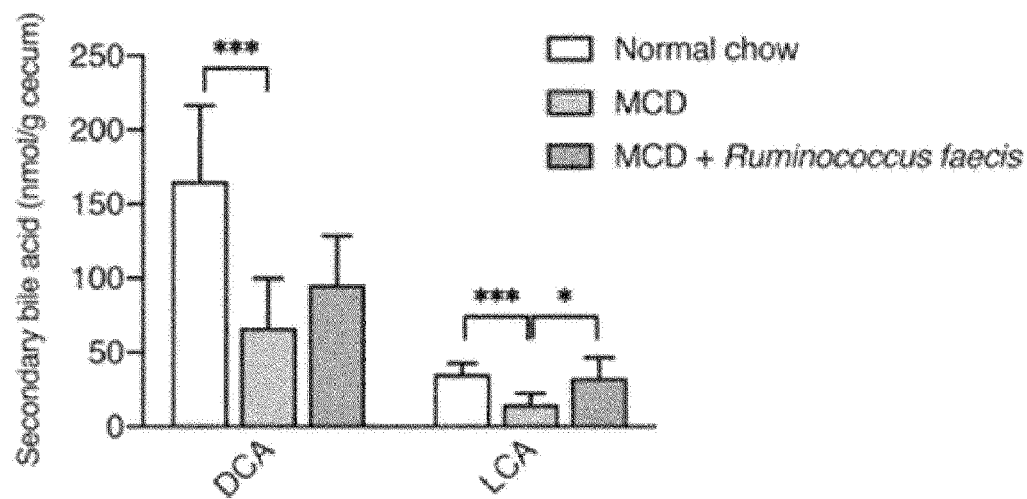

[FIG. 2a]
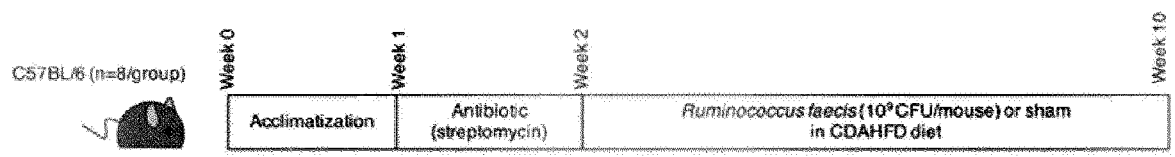
[FIG. 2b]
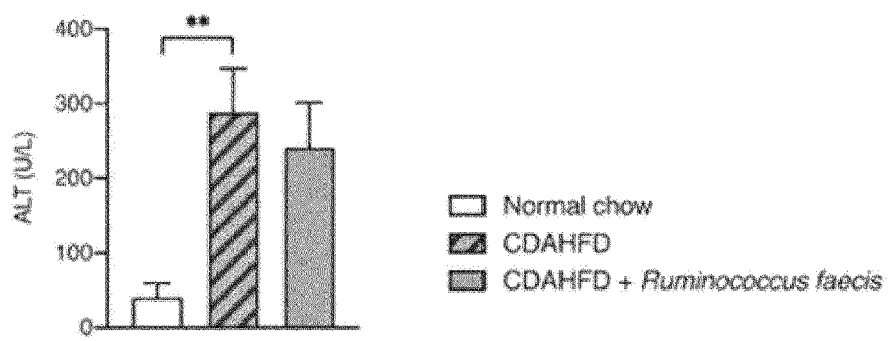
[FIG. 2c]
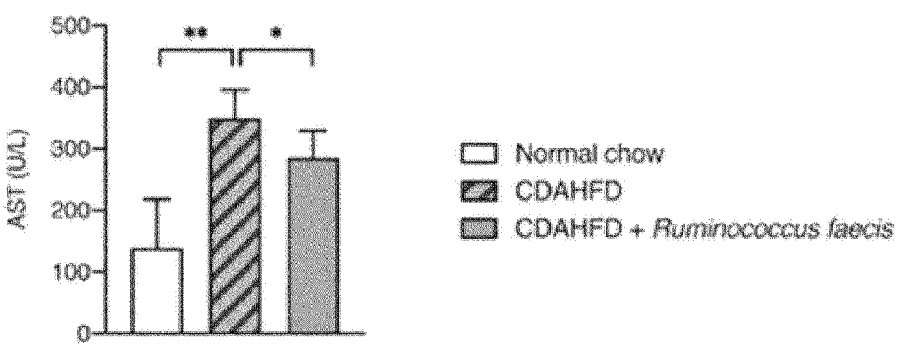

[FIG. 2d]
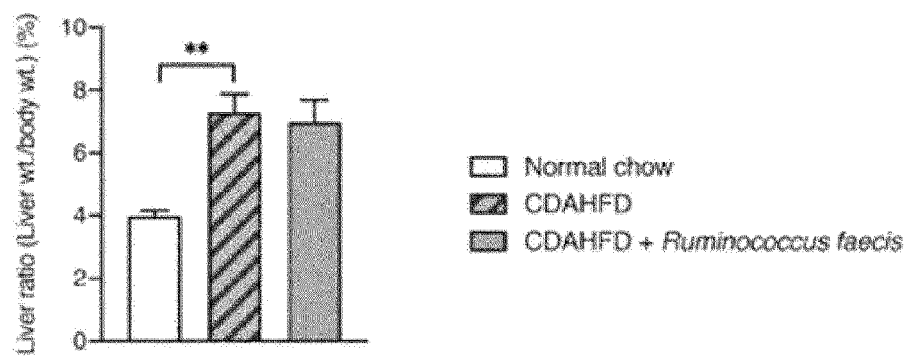

【FIG. 3a】
【FIG. 3b】
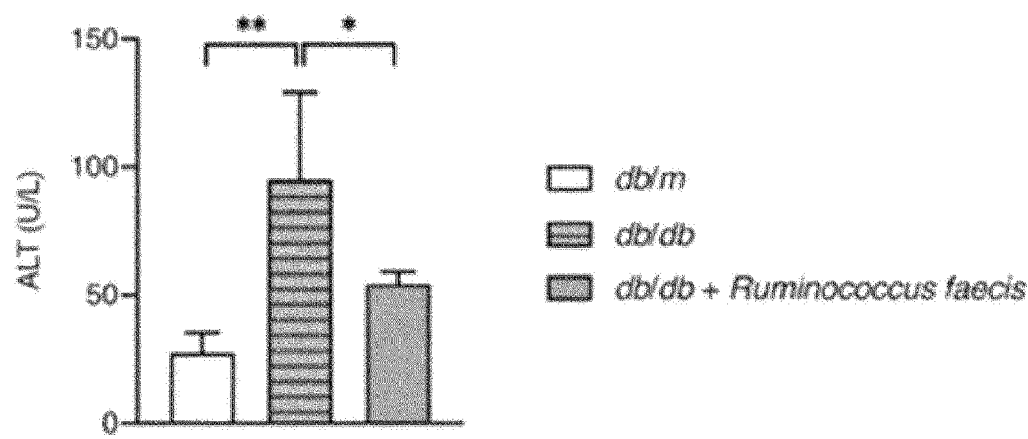
【FIG. 3c】
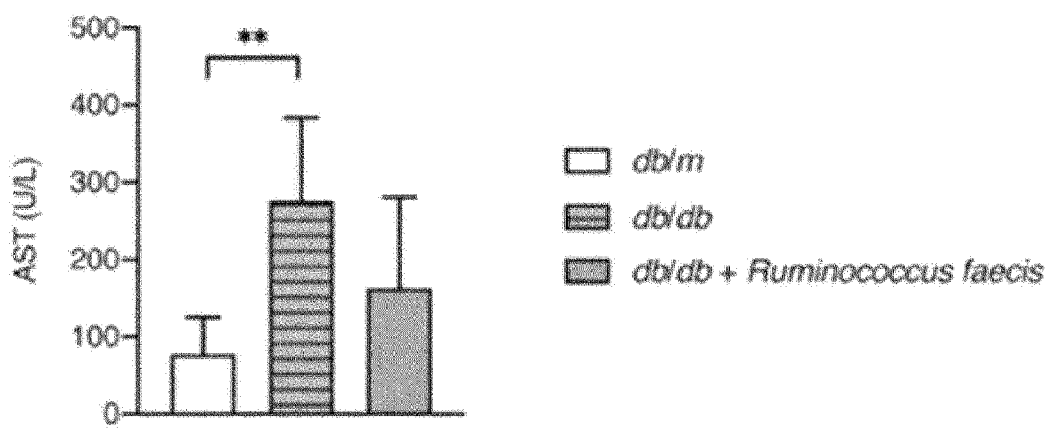

【FIG. 3d】
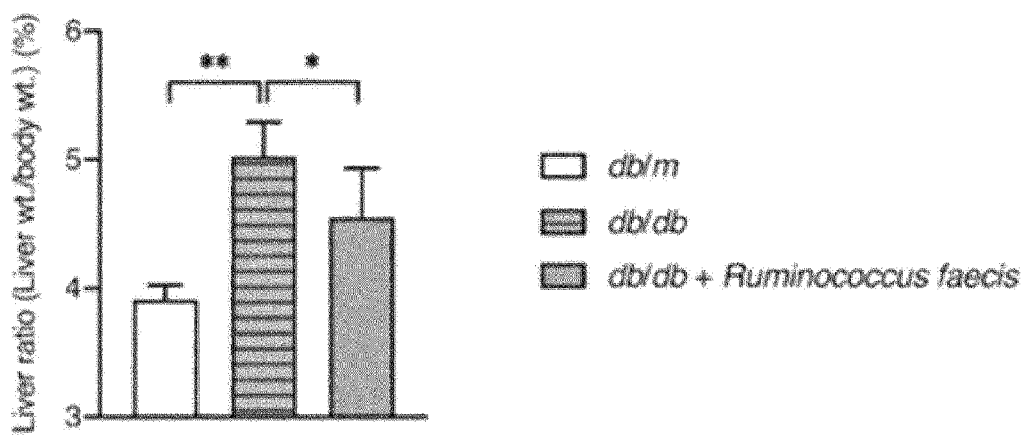
【FIG. 3e】
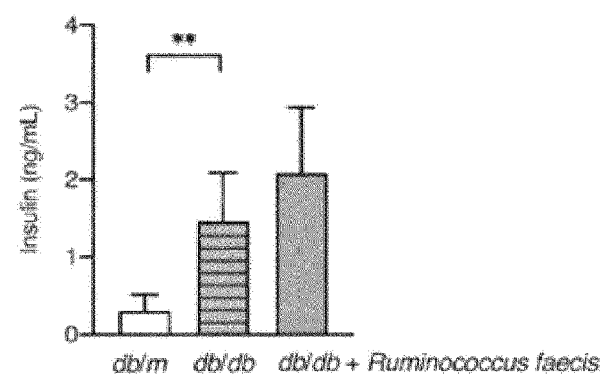
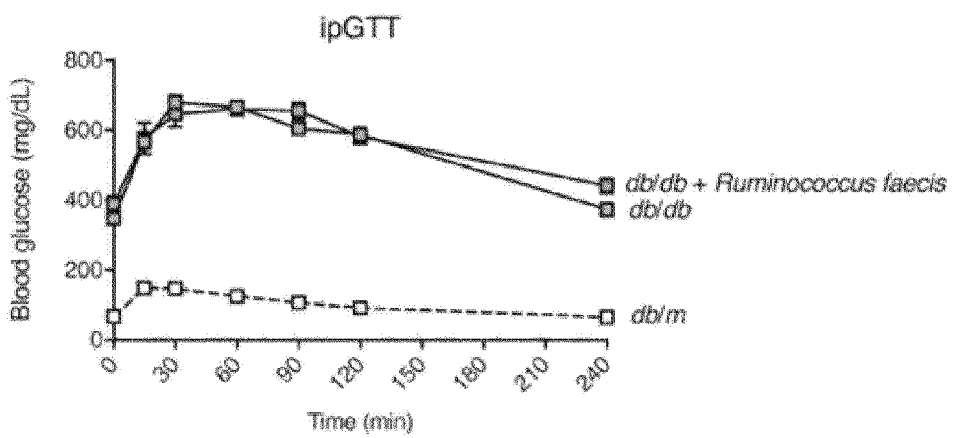

[FIG. 4a]
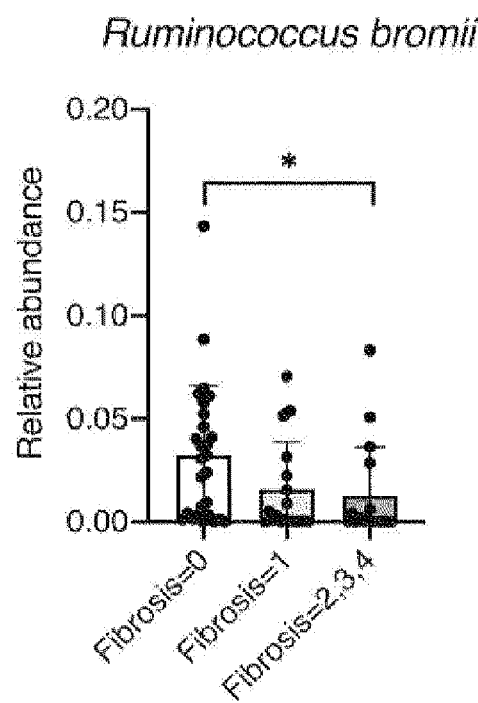

[FIG. 4b]
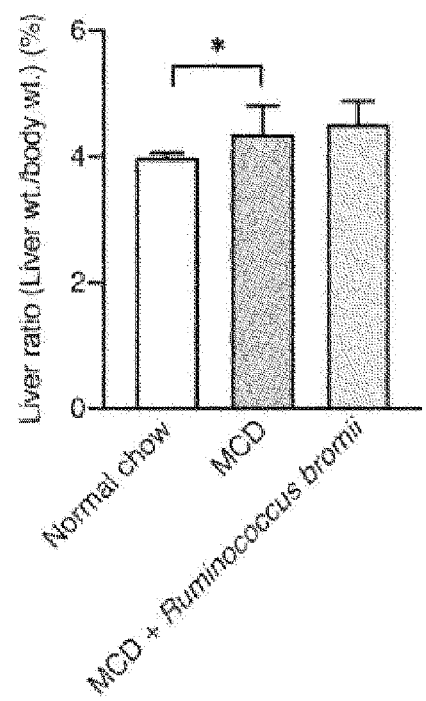

[FIG. 4c]
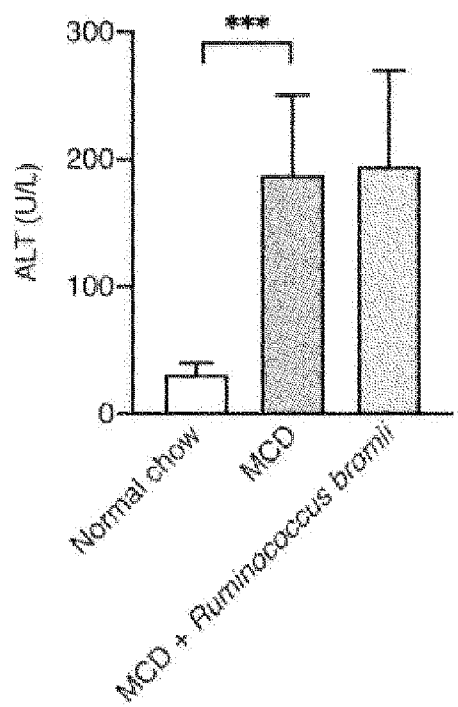

【FIG. 5a】
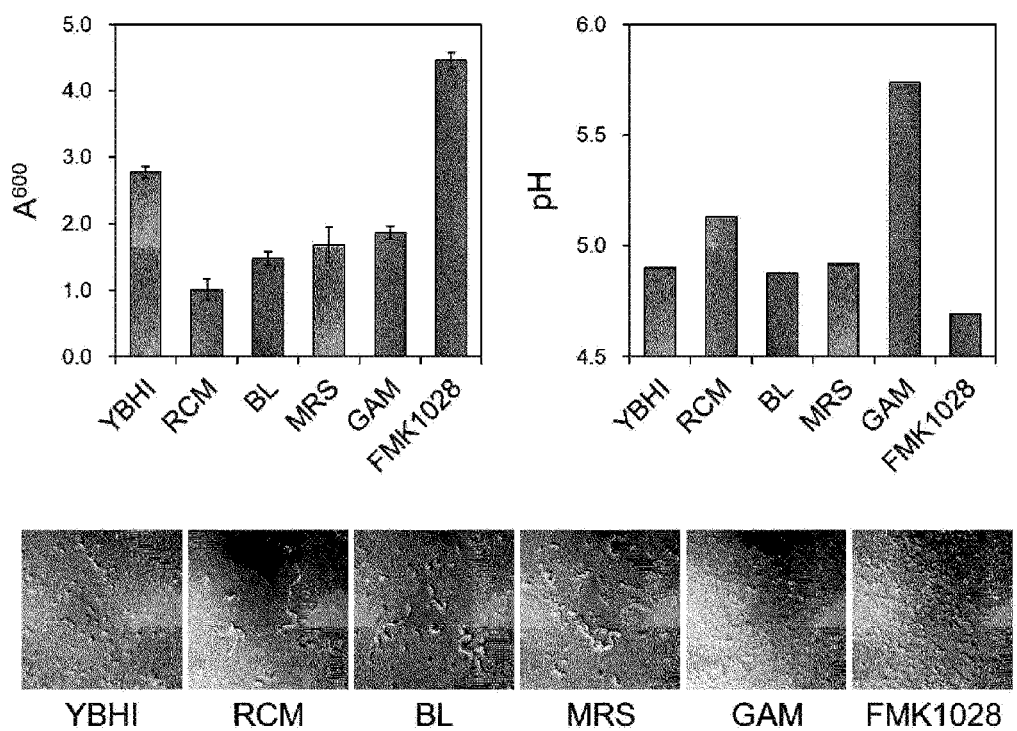
【FIG. 5b】
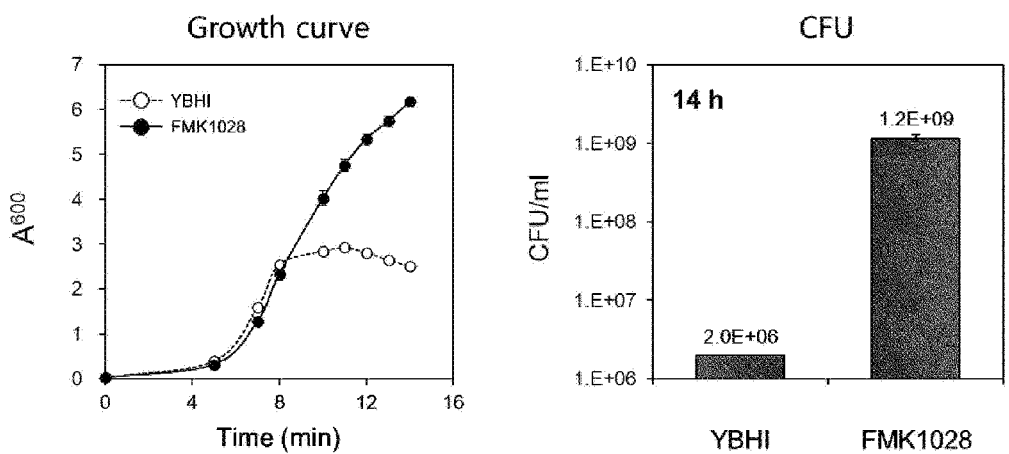

【FIG. 5c】
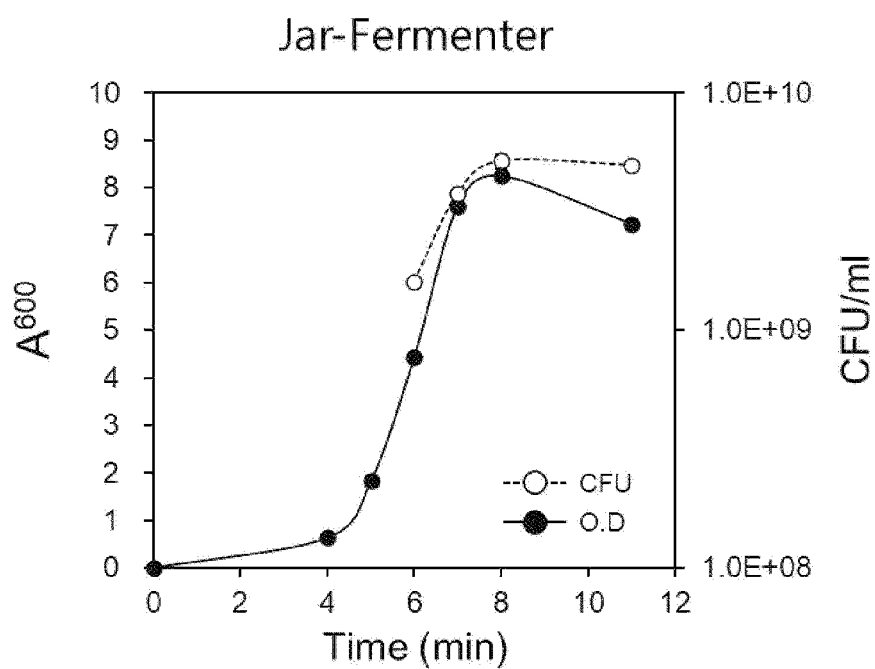

COMPOSITION AND METHOD FOR PREVENTING, ALLEVIATING, OR TREATING LIVER INJURY

TECHNICAL FIELD

The present invention relates to a composition for preventing, alleviating or treating liver injury and a method for preventing, alleviating or treating liver injury.

BACKGROUND ART

Nonalcoholic fatty liver disease (NAFLD) is characterized by liver disease of metabolic disorder leading from simple steatosis, to nonalcoholic steatohepatitis which is an aggressive tissue form that ultimately leads to advanced fibrosis and liver cirrhosis. The global prevalence of NAFLD is estimated to be 24-30% in most epidemiological studies, and is increasing in parallel with obesity and metabolic syndrome.

Recently, increased interest has focused on identifying and understanding specific roles of the intestinal microbiota in various metabolic diseases. Gut dysbiosis, which refers to abnormal changes in the intestinal microbiota compared to the normal microbiota, is related to reduction of bacteria producing beneficial short-chain fatty acid (SCFA), changes in the composition of bile acids, activation of immune reactions to lipopolysaccharide (LPS), an increase of ethanol production by overgrowth of ethanol producing bacteria, and conversion of phosphatidylcholine into choline and trimethylamine Changes in the gut microbiome affecting the gut-liver axis are known to contribute to progression of chronic liver disease such as NAFLD and liver cirrhosis, and advanced fibrosis. However, recovering the abundance of gut microbiome which is enriched or depleted in the disease state does not always alleviate the severity of the disease. Because the changes of the gut microbiome in the disease state might be a result of physiological changes induced by the disease not a cause.

Therefore, there is a need for an effective method for preventing, treating and diagnosing NAFLD, which can determine the histological severity of NAFLD and define changes in the gut microbiome well.

DISCLOSURE

Technical Problem

The present invention is intended to solve the above problems, and an object thereof is to provide a composition for preventing, alleviating or treating liver injury, for example, nonalcoholic fatty liver disease.

Technical Solution

One embodiment of the present invention relates to a composition for preventing, alleviating or treating of liver injury, comprising a *Ruminococcus* spp. strain.

Another embodiment of the present invention relates to a composition for culturing a *Ruminococcus* spp. strain comprising carbon source and nitrogen source.

Other embodiment of the present invention relates to a method for preventing, alleviating or treating liver injury, comprising administering the composition for preventing, alleviating or treating liver injury according to the present invention to a subject in need thereof.

Hereinafter, the present invention will be described in more detail.

One embodiment of the present invention relates to a composition for preventing, alleviating or treating liver injury, comprising a *Ruminococcus* spp. strain. The composition may be a pharmaceutical composition or food composition. The composition may further comprise butyric acid.

The liver injury may be one or more selected from the group consisting of fatty liver, hepatitis, liver fibrosis and liver cirrhosis. The liver injury may be nonalcoholic liver injury. Specifically, the hepatitis may be nonalcoholic steatohepatitis, and the fatty liver may be nonalcoholic fatty liver. The nonalcoholic fatty liver may be non-obese nonalcoholic fatty liver, obese nonalcoholic fatty liver, or diabetic nonalcoholic fatty liver, but not limited thereto. The diabetic nonalcoholic fatty liver may be caused by type 2 diabetes.

Type 2 diabetes patients have nonalcoholic steatohepatitis (NASH) with a 40% chance, and type 2 diabetes patients having nonalcoholic fatty liver has higher prevalence of nonalcoholic steatohepatitis (80.2% vs. 64.4%; p<0.001) and liver fibrosis (40.3% vs. 17.0%; p<0.001) compared to nonalcoholic fatty liver patients without type 2 diabetes. Therefore, there is a need to develop a therapeutic agent for nonalcoholic fatty liver patients having type 2 diabetes. The liver injury with type 2 diabetes is difficult to treat because the prognosis is pooper than that in case of not having type 2 diabetes, however, the composition according to the present invention can treat the liver injury with type 2 diabetes.

The composition may prevent, alleviate or treat liver injury independently of insulin. In the present Examples, as the result of confirming the liver injury effect of the composition according to the present invention using an animal model having insulin resistance, liver injury was significantly alleviated, and thus, it was confirmed that the composition according to the present invention alleviated and treated liver injury independently of insulin.

The composition according to the present invention shows a significantly improved effect of treating liver injury, by being administered to a subject with liver injury. The subject with liver injury may have one or more of characteristics of the following (1) to (5):

(1) increased condition of blood ALT concentration, for example, over 1 time, 1.1 times or more, 1.2 times or more, 1.3 times or more, 1.4 times or more, 1.5 times or more, 1.6 times or more, 1.7 times or more, 1.8 times or more, 1.9 times or more, 2 times or more, 2.1 times or more, 2.2 times or more, 2.3 times or more, 2.4 times or more, 2.5 times or more, 2.6 times or more, 2.7 times or more, 2.8 times or more, 2.9 times or more, 3 times or more, 3.5 times or more, 4 times or more, 4.5 times or more, 5 times or more, 5.5 times or more, 6 times or more, 6.5 times or more, 7 times or more, 7.5 times or more, 8 times or more, 8.5 times or more, 9 times or more, 9.5 times or more, or 10 times or more of the blood ALT concentration of a normal control group.

(2) increased condition of blood AST concentration, for example, over 1 time, 1.1 times or more, 1.2 times or more, 1.3 times or more, 1.4 times or more, 1.5 times or more, 1.6 times or more, 1.7 times or more, 1.8 times or more, 1.9 times or more, 2 times or more, 2.1 times or more, 2.2 times or more, 2.3 times or more, 2.4 times or more, 2.5 times or more, 2.6 times or more, 2.7 times or more, 2.8 times or more, 2.9 times or more, 3 times or more, 3.5 times or more, 4 times or more, 4.5 times or more, 5 times or more, 5.5 times or more, 6 times or more, 6.5 times or more, 7 times or more, 7.5 times or more, 8 times or more, 8.5 times or more, 9 times or more, 9.5 times or more, or 10 times or more of the blood AST concentration of a normal control group.

(3) reduced condition of secondary bile acid concentration in cecum, for example, less than 1 time, 0.9 times or less, 0.8 times or less, 0.7 times or less, 0.6 times or less, 0.5 times or less, 0.4 times or less, 0.3 times or less, 0.2 times or less, or 0.1 times or less of the secondary bile acid concentration in cecum of a normal control group.

(4) increased condition of fibrosis marker gene expression, for example, over 1 time, 1.1 times or more, 1.2 times or more, 1.3 times or more, 1.4 times or more, 1.5 times or more, 1.6 times or more, 1.7 times or more, 1.8 times or more, 1.9 times or more, 2 times or more, 2.1 times or more, 2.2 times or more, 2.3 times or more, 2.4 times or more, 2.5 times or more, 2.6 times or more, 2.7 times or more, 2.8 times or more, 2.9 times or more, 3 times or more, 3.5 times or more, 4 times or more, 4.5 times or more, 5 times or more, 5.5 times or more, 6 times or more, 6.5 times or more, 7 times or more, 7.5 times or more, 8 times or more, 8.5 times or more, 9 times or more, 9.5 times or more, 10 times or more, 11 times or more, 12 times or more, 13 times or more, 14 times or more, 15 times or more, 16 times or more, 17 times or more, 18 times or more, 19 times or more, or 20 times or more overexpressed of the fibrosis marker gene expression of a normal control group, in which the fibrosis marker gene may be one or more selected from the group consisting of Col1a1, Timp1, and α-SMA.

(5) increased condition of liver weight ratio to body weight, for example, over 1 time, 1.1 times or more, 1.2 times or more, 1.3 times or more, 1.4 times or more, 1.5 times or more, 1.6 times or more, 1.7 times or more, 1.8 times or more, 1.9 times or more, 2 times or more, 2.1 times or more, 2.2 times or more, 2.3 times or more, 2.4 times or more, 2.5 times or more, 2.6 times or more, 2.7 times or more, 2.8 times or more, 2.9 times or more, or 3 times or more of the liver weight ratio to body weight of a normal control group.

The normal control group refers to a control group not having liver injury.

In addition, the liver injury of the subject may be one or more selected from the group consisting of fatty liver, hepatitis, liver fibrosis and liver cirrhosis. The liver injury may be nonalcoholic liver injury. Specifically, the hepatitis may be nonalcoholic steatohepatitis, and the fatty liver may be nonalcoholic fatty liver. The nonalcoholic fatty liver may be non-obese nonalcoholic fatty liver, obese nonalcoholic fatty liver, or diabetic nonalcoholic fatty liver, but not limited thereto.

The composition according to the present invention may be administered to a subject with diabetes, and in particular, the composition according to the present invention can prevent, alleviate or treat liver injury independently of insulin, and therefore, it may be administered to a subject with type 2 diabetes.

In the present Examples, as the result of confirming an effect of treating liver injury, for example, nonalcoholic fatty liver, of the composition according to the present invention, the therapeutic effect such as ability of reducing blood ALT concentration, ability of reducing blood AST concentration, ability of reducing the ratio of liver to body weight, and the like, is significantly excellent compared to the therapeutic effect shown in the model without type 2 diabetes, and this means that the composition according to the present invention has an excellent therapeutic effect particularly in a type 2 diabetes subject.

In particular, the therapeutic effect in the subject with type 2 diabetes is more excellent, and the difference in insulin resistance played an important role in the difference in sensitivity related to alleviation or treatment of liver injury by *Ruminococcus*.

The composition according to the present invention may be administered to a subject having liver damage to generate one or more of characteristics of the following (1) to (5):

(1) reducing blood ALT concentration, for example, the blood ALT concentration when the composition is administered is less than 100%, 99% or less, 98% or less, 97% or less, 96% or less, 95% or less, 94% or less, 93% or less, 92% or less, 91% or less, 90% or less, 80% or less, 70% or less, 65% or less, 60% or less, 59% or less, 58% or less, 50% or less, 45% or less, or 40% or less, based on 100% of the blood ALT concentration of the control group not administered with the composition (As one example, in FIG. 1b, when co-administering MCD and *Ruminococcus* faecis strain, 39.21% of ALT level was shown compared to single administration of MCD.)

(2) reducing blood AST concentration, for example, the blood AST concentration when the composition is administered is less than 100%, 99% or less, 98% or less, 97% or less, 96% or less, 95% or less, 94% or less, 93% or less, 92% or less, 91% or less, 90% or less, 80% or less, 70% or less, 65% or less, 64% or less, 63% or less, 62% or less, 61% or less, 60% or less, or 59% or less, based on 100% of the blood AST concentration of the control group not administered with the composition (As one example, in FIG. 1b, when co-administering MCD and *Ruminococcus* faecis strain, 57.52% of AST level was shown compared to single administration of MCD.)

(3) increasing secondary bile acid (for example, cecal secondary bile acid) concentration, for example, the secondary bile acid concentration when the composition is administered is over 100%, 105% or more, 110% or more, 115% or more, 120% or more, 125% or more, 130% or more, 135% or more, 140% or more, 145% or more, 150% or more, 160% or more, 170% or more, 180% or more, 190% or more, or 200% or more, based on 100% of the secondary bile acid concentration of the control group not administered with the composition (As one example, in FIG. 1i, when co-administering MCD and *Ruminococcus* faecis strain, 217.50% of LCA concentration and 143.37% of DCA concentration were shown compared to single administration of MCD.)

(4) reducing fibrotic gene expression, for example, when the composition is administered, the expression of the fibrosis-related gene, for example, one or more of Col1a1, Timp1, and α-SMA, is less than 100%, 99% or less, 98% or less, 97% or less, 96% or less, 95% or less, 94% or less, 93% or less, 92% or less, 91% or less, 90% or less, 80% or less, 78% or less, 75% or less, 70% or less, 65% or less, or 60% or less, based on 100% of the expression of the control group not administered with the composition (As one example, in FIG. 1h, when co-administering MCD and *Ruminococcus* faecis strain, 90.60% of Col1a1 expression, 77.17% of α-SMA expression, and 58.50% of Timp1 expression were shown compared to single administration of MCD.)

(5) reducing liver weight ratio to body weight, for example, the liver weight ratio to body weight when the composition is administered is less than 100%, 99% or less, 98% or less, 97% or less, 96% or less, 95% or less, 94% or less, 93% or less, 92% or less, 91% or less, 90% or less, 89% or less, 88% or less, or 87% or less, based on 100% of the liver weight ratio to body weight of the control group not administered with the composition (As one example, in FIG. 1g, when co-administering MCD and *Ruminococcus* faecis strain, 86.27% of the liver ratio was shown compared to single administration of MCD.)

The control group not administered with the composition refers to a non-administration group which has the same disease, but the composition according to the present invention is not administered thereto.

The secondary bile acid may be one or more selected from the group consisting of deoxycholic acid (DCA), lithocholic acid (LCA), and ursodeoxycholic acid (UDCA).

The fibrotic gene may be one or more selected from the group consisting of Col1a1, Timp1, and α-SMA.

The composition according to the present invention may be administered to a subject having liver injury and having insulin resistance, for example, a subject having type 2 diabetic liver injury, and generate one or more of characteristics of the following (1) to (3):

(1) reduction ratio of the ALT level of over 1 time, 1.1 times or more, 1.2 times or more, 1.3 times or more, 1.4 times or more, 1.5 times or more, 1.6 times or more, 1.7 times or more, 1.8 times or more, 1.9 times or more, 2 times or more, 2.1 times or more, 2.2 times or more, 2.3 times or more, 2.4 times or more, 2.5 times or more, or 2.6 times or more, compared to a control group not having insulin resistance, (2) reduction ratio of the AST level of over 1 time, 1.1 times or more, 1.2 times or more, 1.3 times or more, 1.4 times or more, 1.5 times or more, 1.6 times or more, 1.7 times or more, 1.8 times or more, 1.9 times or more, 2 times or more, 2.1 times or more, or 2.2 times or more, compared to a control group not having insulin resistance, (3) reduction ratio of the liver weight ratio to body weight of over 1 time, 1.1 times or more, 1.2 times or more, 1.3 times or more, 1.4 times or more, 1.5 times or more, 2 times or more, 3 times or more, 4 times or more, 5 times or more, 6 times or more, 7 times or more, 8 times or more, 9 times or more, or 10 times or more, compared to a control group not having insulin resistance.

In the present invention, the term 'active ingredient' means an ingredient which can show desired activity alone or show the activity together with a carrier having no activity by itself.

In the present invention, the term 'prevention' means inhibiting or delaying occurrence of illness, disorder or disease. When the occurrence of illness, disorder or disease is inhibited or delayed during a predetermined period, prevention may be considered complete.

In the present invention, the term 'treatment' means partially or completely alleviating, improving, relieving, inhibiting or delaying a specific illness, disorder and/or disease or symptom according to the disease, and reduce the severity or reduce incidence of one or more symptoms or characteristics.

The pharmaceutical composition of the present invention may further comprise one or more of active ingredients showing the same or similar function in addition to the active ingredient.

In addition, the pharmaceutical composition according to the present invention may be prepared in a unit dose form or prepared by being inserted into a multidose container, by formulating it using a pharmaceutically acceptable carrier, according to a method which may be clearly conducted by those skilled in the art to which the present invention pertains. In the present invention, the term 'carrier' means a compound that facilitates addition of a compound into a cell or tissue, and the term 'pharmaceutically acceptable' refers to a composition which is physiologically acceptable and when administered to a human, generally, does not cause an allergic reaction such as gastrointestinal disorder, dizziness or a similar reaction thereto.

The pharmaceutically acceptable carrier is commonly used in formulation, and it comprises lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxylbenzoate, propyl hydroxybenzoate, talc, magnesium stearate, and mineral oil, and the like, but not limited thereto.

In addition, the pharmaceutical composition according to the present invention may further comprise an additive such as a filler, an anti-coagulant, a lubricant, a wetting agent, a flavoring, an emulsifier, a preservative, and the like, in addition to the ingredients. In the present invention, the content of the additive comprised in the pharmaceutical composition may not be particularly limited, and it may be appropriately adjusted within the content range used in common formulation.

Furthermore, the pharmaceutical composition according to the present invention may be formulated in an oral formulation. The non-limitative examples of the oral formulation may comprise tablets, troches, lozenge, aqueous suspension, oily suspension, formulated powder, granules, emulsion, hard capsules, soft capsules, syrup or elixirs, or the like. In order to formulate the pharmaceutical composition according to the present invention for oral administration, a binder such as lactose, saccharose, sorbitol, mannitol, starch, amylopectin, cellulose or gelatin; an excipient such as dicalcium phosphate; a disintegrating agent such as corn starch or sweet potato starch; magnesium stearate, calcium stearate, sodium stearyl fumarate, and the like may be used, and a sweetener, a flavoring agent, a syrup, and the like may also be used. Moreover, in case of capsules, a liquid carrier such as fat oil, and the like may be further used in addition to the aforementioned substances.

In the present invention, the term 'excipient' means any substance, which is not a therapeutic agent, and refers to one which is used as a carrier or medium for delivery of a therapeutic agent or is added to a pharmaceutical composition. Thereby, it may improve handling and storage characteristics or allow and facilitate dosage unit formation of the composition.

The pharmaceutical composition according to the present invention may be used by being formulated in various forms such as oral formulations comprising liquid, suspension, powder, granules, tablets, capsules, pills, extract, emulsion, syrup, aerosol, and the like, and injections of sterile injection solution, and it may be orally administered, or be administered through various routes comprising intravenous, intraperitoneal, subcutaneous, intrarectal, and topical administration, and the like. In the present invention, the term 'oral administration' means that an active ingredient is administered to the gastrointestinal tract for absorption, that is, a substance prepared for digestion.

A preferable dosage of the pharmaceutical composition according to the present invention may have various ranges depending on the patient's condition and body weight, age, gender, health status, dietary constitution specificity, properties of a formulation, degree of disease, administration time of the composition, administration method, administration period or interval, excretion rate and drug form, and may be appropriately selected by those skilled in the art.

In the present invention, the term 'effective dosage of a pharmaceutical composition' refers to an amount of the composition of an active ingredient sufficient to treat a specific symptom. This may vary depending on the formulation method, administration method, administration time and/or administration route of the pharmaceutical composition, and this may vary depending on various factors comprising the type or degree of the response to be achieved by administration of the pharmaceutical composition, the type, age, body weight, general health status, symptoms or degree of disease, gender, diet, excretion of a subject to be administered, and components of drugs or other compositions used together simultaneously or at once to the corresponding subject, and similar factors well-known in the pharmaceutical field, and those skilled in the art may readily determine and prescribe an effective dosage for desired treatment.

The administration of the pharmaceutical composition according to the present invention may be administered once a day, and may be administered divided into several times. The composition may be administered as an individual therapeutic agent or administered in combination with other therapeutic agents, and may be administered sequentially or simultaneously with conventional therapeutic agent. Taking all of the above factors into consideration, it may be administered in an amount that can obtain the maximum effect with a minimum amount without side effects.

For example, the composition according to the present invention may be administered in a daily dose of 0.001 to 10,000 mg, 0.001 to 5,000 mg, 0.001 to 1,000 mg, 0.001 to 500 mg, 0.001 to 300 mg, 0.001 to 100 mg, 0.001 to 50 mg, 0.001 to 30 mg, 0.001 to 10 mg, 0.001 to 5 mg, 0.001 to 1 mg, 0.001 to 0.5 mg, 0.001 to 0.1 mg, 0.001 to 0.05 mg, 0.001 to 0.01 mg, 0.01 to 10,000 mg, 0.01 to 5,000 mg, 0.01 to 1,000 mg, 0.01 to 500 mg, 0.01 to 300 mg, 0.01 to 100 mg, 0.01 to 50 mg, 0.01 to 30 mg, 0.01 to 10 mg, 0.01 to 5 mg, 0.01 to 1 mg, 0.01 to 0.5 mg, 0.01 to 0.1 mg, 0.01 to 0.05 mg, 0.1 to 10,000 mg, 0.1 to 5,000 mg, 0.1 to 1,000 mg, 0.1 to 500 mg, 0.1 to 300 mg, 0.1 to 200 mg, 0.1 to 100 mg, 0.1 to 50 mg, 0.1 to 30 mg, 0.1 to 10 mg, 0.1 to 5 mg, 0.1 to 1 mg, 0.1 to 0.5 mg, 1 to 10,000 mg, 1 to 5,000 mg, 1 to 1,000 mg, 1 to 500 mg, 1 to 300 mg, 1 to 200 mg, 1 to 100 mg, 1 to 50 mg, 1 to 10 mg, 1 to 5 mg, 10 to 10,000 mg, 10 to 5,000 mg, 10 to 1,000 mg, 10 to 500 mg, 10 to 300 mg, 10 to 200 mg, 10 to 100 mg, 10 to 50 mg, 10 to 40 mg, 10 to 30 mg, 10 to 20 mg, 100 to 10,000 mg, 100 to 5,000 mg, 100 to 1,000 mg, 100 to 500 mg, 100 to 300 mg, or 100 to 200 mg per 1 kg body weight, but not limited thereto. As one example, the daily dose of the composition according to the present invention may be 0.001 to 10 g/l day, 0.001 to 5 g/l day, 0.01 to 10 g/l day, or 0.01 to 5 g/l day, based on oral administration of an adult patient. In addition, the total daily dose may be divided and administered continuously or non-continuously if necessary.

The composition according to the present invention may further comprise a freeze-drying protective agent. The freeze-drying protective agent may comprise one or more selected from the group consisting of monosaccharides, disaccharides, polysaccharides, carbohydrates, minerals, amino acids, sucrose, calcium phosphate, arginine, sodium chloride, fructose, potassium phosphate monobasic, potassium phosphate dibasic and trehalose.

The sucrose may be added to the freeze-drying protective agent by 100 to 300 g/L, 100 to 250 g/L, 100 to 200 g/L, 150 to 300 g/L, 150 to 250 g/L, 150 to 200 g/L, 200 to 300 g/L, or 200 to 250 g/L, and as one example, it may be added by 200 g/L.

The calcium phosphate may be added to the freeze-drying protective agent at a concentration of 5 to 20 g/L, 5 to 15 g/L, 5 to 12 g/L, 5 to 11 g/L, 7 to 20 g/L, 7 to 15 g/L, 7 to 12 g/L, 7 to 11 g/L, 10 to 20 g/L, 10 to 15 g/L, 10 to 12 g/L, or 10 to 11 g/L, and as one example, it may be added by 10.5 g/L.

The amino acid may be added to the freeze-drying protective agent at a concentration of 1 to 10 g/L, 1 to 8 g/L, 1 to 6 g/L, 1 to 5 g/L, 3 to 10 g/L, 3 to 8 g/L, 3 to 6 g/L, 3 to 5 g/L, 4 to 10 g/L, 4 to 8 g/L, 4 to 6 g/L, or 4 to 5 g/L, and as one example, it may be added by 4 g/L.

The sodium chloride may be added to the freeze-drying protective agent at a concentration of 0.1 to 5 g/L, 0.1 to 3 g/L, 0.1 to 1 g/L, 0.5 to 5 g/L, 0.5 to 3 g/L, or 0.5 to 1 g/L, and as one example, it may be added by 0.8 g/L.

The *Ruminococcus* spp. strain according to the present invention may be *Ruminococcus* faecis. As one example, the *Ruminococcus* spp. strain may be *Ruminococcus* faecis having accession number KCTC no. 5757. In the present description, the *Ruminococcus* faecis having accession number KCTC no. 5757 may be represented by *Ruminococcus* faecis KBL1028.

The strain may continue to grow after 8 hours of culturing, 9 hours of culturing, 10 hours of culturing, 11 hours of culturing, 12 hours of culturing, 13 hours of culturing, or 14 hours of culturing, in a culture medium with a carbon source concentration of 5 to 30% (w/v), a nitrogen source concentration of 50 to 90% (w/v), a mineral concentration of 5 to 15% (w/v), and an amino acid concentration of 0.1 to 10% (w/v).

The strain may have excellent culture efficiency in FMK1028 medium having the composition according to Table 3. For example, the strain may be characterized that absorbance after cultured in FMK1028 medium having the composition according to Table 3 is higher than absorbance after culture in one or more selected from the group consisting of YBHI medium, GAM medium, MRS medium, BL medium, and RCM medium. As one example, the strain may be one in which the number of viable cells per unit volume after 14 hours of culturing in FMK1028 medium having the composition according to Table 3 is 10 times or more, 50 times or more, 100 times or more, 150 times or more, 200 times or more, 250 times or more, 300 times or more, 350 times or more, 400 times or more, 450 times or more, 500 times or more, 550 times or more, or 600 times or more, when cultured in YBHI medium.

Other embodiment of the present invention relates to a composition for culturing a *Ruminococcus* spp. strain comprising carbon source and nitrogen source. The carbon source may be one or more selected from the group consisting of glucose, sucrose, fructose, lactose, maltose, molasses and galactose. The nitrogen source may be one or more selected from the group consisting of yeast extract, soy peptone, skim milk, tryptone, casamino acids, potato peptone, pea peptone, wheat peptone, broadbean peptone, papaic soy peptone, and lupin peptone.

Other embodiment of the present invention relates to a composition for culturing a *Ruminococcus* spp. strain, comprising carbon source and nitrogen source. The carbon source may be at a concentration of 5 to 30% (w/v), and the nitrogen source may be at a concentration of 50 to 90% (w/v). The *Ruminococcus* spp. strain is as described above.

The carbon source may comprise one or more selected from the group consisting of glucose, sucrose, fructose, lactose, maltose, molasses and galactose.

The nitrogen source may comprise one or more selected from the group consisting of yeast extract, soy peptone, skim milk, tryptone, casamino acids, potato peptone, pea peptone, wheat peptone, broadbean peptone, papaic soy peptone, and lupin peptone.

The composition for culturing a *Ruminococcus* spp. strain may facilitate growth after 8 hours, 9 hours, 10 hours, 11 hours, 12 hours, 13 hours or 14 hours of culturing of the *Ruminococcus* spp. strain.

The composition for culturing a *Ruminococcus* spp. strain may further comprise one or more selected from the group consisting of minerals, amino acids, vitamins, nucleic acids, and inorganic salts.

The mineral may comprise one or more selected from the group consisting of sodium acetate, sodium chloride, sodium phosphate monobasic, sodium phosphate dibasic, potassium chloride, magnesium sulfate, and manganese sulfate.

The amino acid may comprise L-cysteine, L-leucine, L-isoleucine, L-valine, L-tryptophan, L-threonine, L-phenylalanine, and L-methionine.

The concentration of the carbon source may be 5 to 30% (w/v), and the concentration of the nitrogen source may be 50 to 90% (w/v), and the concentration of the mineral may be 5 to 15% (w/v), and the concentration of the amino acid may be 0.1 to 10% (w/v).

Other embodiment of the present invention relates to a method for culturing a *Ruminococcus* spp. strain, comprising inoculating a *Ruminococcus* spp. strain to the composition for culturing a *Ruminococcus* spp. strain according to the present invention, and culturing it.

The method for culturing may facilitate growth after 8 hours, 9 hours, 10 hours, 11 hours, 12 hours, 13 hours or 14 hours of culturing of the *Ruminococcus* spp. strain.

The culturing may be a static culture, a fed-batch culture or a batch culture, but not limited thereto.

Other embodiment of the present invention relates to a method for preventing, alleviating or treating liver injury, comprising administering the composition for preventing, alleviating or treating liver injury according to the present invention to a subject in need thereof. The composition may comprise a *Ruminococcus* spp. strain. The composition for preventing, alleviating or treating liver injury, the *Ruminococcus* spp. strain and the like are as described above. The subject is a subject having liver injury, and the subject having liver injury is as described above. For example, the subject having liver injury may be a subject having insulin resistance, and as one example, it may be a subject having diabetes, specifically, a subject having type 2 diabetes.

Advantageous Effects

The pharmaceutical composition for preventing or treating of the present invention can be effectively used for treatment of liver injury, for example, nonalcoholic fatty liver disease.

BRIEF DESCRIPTION OF THE DRAWINGS

FIG. 1*a* is a drawing which shows the experimental process to investigate the effect for treating liver injury according to administration of *Ruminococcus* faecis in the liver injury animal model induced by the MCD diet.

FIG. 1*b* is a drawing which shows the result of ALT and AST measurement according to administration of *Ruminococcus* faecis in the liver injury animal model induced by the MCD diet.

FIG. 1*c* to FIG. 1*e* are drawings which show that the histological severity of liver injury induced by the MCD diet is significantly alleviated in mice fed with *Ruminococcus* faecis, and FIG. 1*c* is a drawing which shows that the liver tissue is alleviated according to administration of *Ruminococcus* faecis by H&E (top) and Sirius red (bottom) staining methods.

FIG. 1*d* is a drawing which quantifies pathological alleviation by administration of *Ruminococcus* faecis using NAFLD activity scores.

FIG. 1*e* is a drawing which shows collagen distribution in liver alleviated by administration of *Ruminococcus* faecis.

FIG. 1*f* is a drawing which shows the changes in the body weight by the MCD diet.

FIG. 1*g* is a drawing which shows the liver ratio in the body weight when administering *Ruminococcus* faecis (MCD+*R. faecis*) compared to the control administered group mice (MCD).

FIG. 1*h* is a drawing which shows that the markers of fibrosis generation and proliferation are alleviated according to administration of *Ruminococcus* faecis.

FIG. 1*i* is a drawing which shows that the topical level of secondary bile acid (DCA and LCA) reduced by the MCD diet is increased by treatment of *Ruminococcus* faecis.

FIG. 2*a* is a drawing which shows the experimental process to investigate the effect for treating liver injury according to administration of *Ruminococcus* faecis in the liver injury animal model induced by the CDAHFD diet.

FIG. 2*b* is a drawing which shows that the ALT level is reduced according to administration of *Ruminococcus* faecis in the liver injury animal model induced by the CDAHFD diet.

FIG. 2*c* is a drawing which shows the AST level is reduced according to administration of *Ruminococcus* faecis in the liver injury animal model induced by the CDAHFD diet.

FIG. 2*d* is a drawing which shows the liver weight ratio to the body weight according to administration of *Ruminococcus* faecis in the liver injury animal model induced by the CDAHFD diet.

FIG. 3*a* is a drawing which shows the experimental process to investigate the effect for treating liver injury according to administration of *Ruminococcus* faecis in the genetic leptin-deficient animal model.

FIG. 3*b* is a drawing which shows that the ALT level is reduced according to administration of *Ruminococcus* faecis in the genetic leptin-deficient animal model.

FIG. 3*c* is a drawing which shows that the AST level is reduced according to administration of *Ruminococcus* faecis in the genetic leptin-deficient animal model.

FIG. 3*d* is a drawing which shows that the liver weight ratio to the body weight is reduced according to administration of *Ruminococcus* faecis in the genetic leptin-deficient animal model.

FIG. 3*e* is a drawing which shows the serum fasting insulin level and insulin resistance measured by ipGTT in the genetic leptin-deficient animal model.

FIG. 4*a* is a drawing which shows that *Ruminococcus bromii* is significantly reduced in the liver fibrosis disease group.

FIG. 4b is a drawing which shows the liver ratio level in the body weight according to administration of *Ruminococcus bromii*.

FIG. 4c is a drawing which shows the ALT level according to administration of *Ruminococcus bromii*.

FIG. 5a is a drawing which shows the result of comparing the cultivation potential of *Ruminococcus* faecis and cell morphology in YBHI medium, RCM medium, BL medium, MRS medium, GAM medium, or FMK1028 medium.

FIG. 5b is a drawing which shows the growth curve of *Ruminococcus* faecis and the viable cell count per unit volume.

FIG. 5c is a drawing which shows the growth curve of *Ruminococcus* faecis cultured in a fermenter and the viable cell count.

MODE FOR INVENTION

Hereinafter, the present invention will be described in more detail by the following Examples. However, these Examples are intended to illustrate the present invention only, but the scope of the present invention is not limited by these Examples.

Example 1: Test for Liver Injury Treatment Using Experimental Animals (1) Preparation of Experimental Animals

*Ruminococcus faecis* (KCTC no. 5757 deposited on Jan. 21, 2009 with the Korean Collection for Type Cultures. Korea Research Institute of Bioscience and Biotechnology (KRIBB), 181, Ipsin-gil, Jeongeup-si, Jeollabuk-do 56212. Republic of Korea) was distributed from Korea Research Institute of Bioscience and Biotechnology, Korean Collection for Type Cultures (KCTC, Jeollabuk-do, Republic of Korea), and cultured in YBHI medium under an anaerobic condition, and collected after 24 hours, and washed using PBS (+0.5% cysteine) twice, and then fed orally. 6-old male C57BL/6N mice (Orient Bio, Gyeonggi-do, Republic of Korea) were bred at Seoul National University's general animal facility according to university guidelines as experimental animals, and all animal experiments were approved by Institutional Animal Care and Use Committee of Seoul National University.

In order to proceed with the NAFLD animal model experiment induced by the MCD diet, 1 week after adapting the mice to a standard chow diet, streptomycin was treated to drinking water at a concentration of 1 g/L for intestinal settlement of *Ruminococcus* faecis and watered for 1 week. For 5 weeks thereafter, mice were fed a methionine and choline deficient L-amino acid diet (MCD) (Research diet, New Brunswick, NJ, USA; Cat. no.: A02082002B) at the same time, and one of *Ruminococcus* faecis suspended so as to contain $10^9$ CFU in 200 μL PBS or control PBS (sham) was orally administered daily (FIG. 1a). After 5 weeks of administration, mice were euthanized and biochemical analysis, anatomical analysis, confirmation of expression of markers of liver fibrosis occurrence and proliferation, and bile acid analysis were performed.

(2) Biochemical Analysis

Serum alanine aminotransferase (ALT) and aspartate aminotransferase (AST) levels were measured with Fuji DRI-CHEM 3500i biochemical analyzer (FujiFilm, Tokyo, Japan). The ALT and AST measuring results were shown in FIG. 1b.

(3) Anatomical Analysis

After euthanasia, liver samples were excised and fixed in 10% formalin solution (Sigma-Aldrich, St. Louis, MO, USA). Hematoxylin and eosin (H&E) and Sirius red staining were performed at LOGONE Bio Convergence Research Foundation (Seoul, Republic of Korea). Stained whole slide images were analyzed using Pannoramic Viewer (3DHISTECH, Budapest, Hungary). In order to calculate the collagen proportionate area, 8 images per group were randomly selected and analyzed using ImageJ software (NIH, Bethesda, MdD USA; http://imagej.nih.gov/ij).

In addition, for the ratio of liver to body weight, the body weight of mice administered with *Ruminococcus* faecis for 5 weeks and the weight of liver were measured and then the ratio of the liver weight to the body weight was calculated. The result of measuring the body weight of mice was shown in FIG. 1f, and the ratio of the liver weight to the body weight was shown in FIG. 1g.

(4) Confirmation of Expression of Markers of Liver Fibrosis Occurrence and Proliferation Total RNA of liver samples was extracted using Easy-spin™ Total RNA Extraction kit (iNtRON Biotechnology, Gyeonggi-do, Republic of Korea), and reverse transcribed into cDNA using High Capacity RNA-to-cDNA kit (Thermo Fisher Scientific, Waltham, MA, USA). Quantitative PCR was performed using SYBR™ Green qPCR Master Mix (Thermo Fisher Scientific, Waltham, MA, USA) and Applied Biosystems™ QuantStudio™ 6 Flex qPCR system (Thermo Fisher Scientific, Waltham, MA, USA). The sequences of used primers were as follows.

TABLE 1

| Gene name | Primer category | Sequences | SEQ ID NO. |
| --- | --- | --- | --- |
| Cyclophilin A | Forward | 5'-TGGAGAGCACCAAGACAGACA-3' | 1 |
| | reverse | 5'-TGCCGGAGTCGACAATGAT-3' | 2 |
| Col1a1 | forward | 5'-ACCTGTGTGTTCCCTACTCA-3' | 3 |
| | reverse | 5'-GACTGTTGCCTTCGCCTCTG-3' | 4 |
| Timp1 | forward | 5'-TGCCTGCTGCGATTACAACC-3' | 5 |
| | reverse | 5'-GGAATGGTGTGGTGATGCATGG-3' | 6 |
| α-SMA | forward | 5'-GGCTCTGGGCTCTGTAAGG-3' | 7 |
| | reverse | 5'-CTCTTGCTCTGGGCTTCATC-3' | 8 |

(5) Bile Acid Analysis

After extracting cecum of mice, 80% methanol corresponding to a volume ratio of 10 times was added and mixed. For bile acid extraction, samples were pulverized with a sonicator for 3 minutes and then stored under a condition of 4° C. for 24 hours. Then, 100% methanol 1 mL was added to the supernatant obtained by centrifugation and secondary extraction was progressed using a bead beating machine under a condition of 15 frequency and 30 minutes. Methanol in which bile acid was dissolved evaporated all liquid substances by vacuum drying under a condition of 30° C. and 24 hours, and remaining solid substances were dissolved using 55% methanol. The extracted bile acid was placed in a dedicated tube and then measured using Micromass® Q-ToF mass spectrometer (Waters Technologies, Milford, MA, USA).

(6) Experimental Result

When *Ruminococcus* faecis was administered (MCD+*R. faecis*), compared to the control-administered mice (MCD), the ALT and AST levels were reduced (FIG. 1*b*).

As the result of anatomical and histological analysis, the histological seriousness of NAFLD induced by the MCD diet was significantly improved in mice fed with *Ruminococcus* faecis (FIG. 1*c* to FIG. 1*e*). The MCD diet caused dramatic body weight loss as known in the previous document, and administration of *Ruminococcus* faecis did not affect the body weight (FIG. 1*f*). However, when *Ruminococcus* faecis was administered (MCD+*R. faecis*), compared to the control-administered mice (MCD), the liver ratio in the body weight was reduced (FIG. 1*g*).

As the result of confirming the expression of markers of liver fibrosis occurrence and proliferation, the markers of liver fibrosis occurrence and proliferation were significantly alleviated in mice fed with *Ruminococcus* faecis (Timp1, p=0.0018; α-SMA, p=0.0330) (FIG. 1*h*).

In parallel with changes in biochemical and histological liver injury markers, the local level of secondary bile acid (DCA and LCA) was also reduced by the MCD diet and increased by treatment of *Ruminococcus* faecis (FIG. 1*i*).

Such result shows that there is a protective effect for liver fibrosis in the *Ruminococcus* faecis MCD diet mouse model.

Example 2: Liver Injury Treatment Test Using Animal Model

In order to confirm an alleviation effect of *Ruminococcus* faecis for liver injury by nonalcoholic fatty liver, a choline-deficient, L-amino acid-defined, high-fat diet (CDAHFD) diet mouse model preventing body weight loss and not showing insulin resistance was used.

Choline plays a role in accumulating and releasing triglycerides in hepatocytes in a form of VLDL, but choline is lacking in the CDAHFD diet, and therefore it is a diet model in which triglycerides from a high-fat diet accumulate in hepatocytes to induce fatty liver, and unlike the MCD model, body weight loss does not occur and liver fibrosis is more severely induced. However, it is known that the CDAHFD model does not induce insulin resistance.

Specifically, as shown in FIG. 2*a*, one week after C57BL/6N mice were adapted to a standard chow diet, streptomycin (1 g/L) was dissolved in drinking water and fed for one week for intestinal settlement of *Ruminococcus* faecis. After that, for 8 weeks, a CDAHFD (choline-deficient, L-amino acid-defined, high-fat diet) diet lacking choline and containing 60% fat was fed, and 200 μL of either *Ruminococcus* faecis suspended so that $10^9$ CFU was added in 200 μL PBS or control PBS (sham) was orally administered daily. After 8 weeks of administration, mice were euthanized and serum biochemical analysis and anatomical analysis were performed. As a biochemical analysis, ALT and AST analysis was performed in the same manner as in Example 1, and the liver ratio to the body weight was measured in the same manner as in Example 1.

As shown in FIG. 2*b* to FIG. 2*d*, the ALT and AST levels were reduced according to administration of *Ruminococcus* faecis (FIG. 2*b* and FIG. 2*c*), but there was no significant difference in the liver ratio to the body weight by administration of *Ruminococcus* faecis (FIG. 2*d*). This means that *Ruminococcus* faecis has a therapeutic effect for nonalcoholic fatty liver injury induced by the CDAHFD feed, but that there was no significant difference in the liver ratio to the body weight means that fats accumulated in the liver were not significantly reduced.

Example 3: Liver Injury Treatment Test Using Genetic Leptin-Deficient Model

In order to confirm whether a therapeutic effect for nonalcoholic fatty liver disease by *Ruminococcus* faecis is generated in case of having insulin resistance, a genetic leptin-deficient (db/db) model causing spontaneous diabetes with insulin resistance and fatty liver is used to confirm a therapeutic effect of *Ruminococcus* faecis on nonalcoholic fatty liver disease. As a control group of the db/db model, db/m was used, which corresponds to the heterozygote of db allele.

The db/db model is a model having a mutation in a leptin receptor, obesity and insulin resistance are induced, resulting in hyperglycemia, and is often used as a model for type 2 diabetes. The db/db model is known as steatosis is rapidly induced, but it is known as steatohepatitis (NASH) and liver fibrosis are not easily induced.

Specifically, as shown in FIG. 3*a*, one week after db/db model mice were adapted to a standard chow diet, streptomycin (1 g/L) was dissolved in drinking water and fed for one week for intestinal settlement of *Ruminococcus* faecis. After that, for 5 weeks, a common diet was fed, and 200 μL of either *Ruminococcus* faecis suspended so that $10^9$ CFU was added in 200 μL PBS or control PBS (sham) was orally administered daily. After 5 weeks of administration, mice were euthanized and biochemical analysis and anatomical analysis were performed. As the biochemical analysis, the ALT and AST analysis was performed by the substantially same method as the Example 1, and the liver ratio to the body weight was measured by the substantially same method as the Example 1.

Serum fasting insulin levels measured by ipGTT in db/db mice were measured using Ultra Sensitive Mouse Insulin ELISA kit (Crystal Chem, Elk Grove Village, IL, USA). The intraperitoneal glucose tolerance test to confirm insulin resistance was conducted at the $3^{rd}$ week of administration of *Ruminococcus* faecis, and after 16 hours of dietary restriction other than water, a glucose solution was administered intraperitoneally so that 1 g of glucose per 1 kg of body weigh was administered. Thereafter, blood glucose was measured using Accu-Chek® Performa blood glucose meter (Roche Diagnostics, Risch-Rotkreuz, Switzerland) at a predetermined time.

As shown in FIG. 3*b* to FIG. 3*d*, the ALT and AST levels were reduced according to administration of *Ruminococcus* faecis (FIG. 3*b* and FIG. 3*c*), and in particular, the liver ratio to the body weight was also significantly reduced (FIG. 3*d*). Nevertheless, as shown in FIG. 3*e*, the serum fasting insulin level and insulin resistance measured by ipGTT in db/db mice were not affected by treatment of *Ruminococcus* faecis.

*Ruminococcus* faecis also showed a therapeutic effect for nonalcoholic fatty liver disease in the db/db model having insulin resistance, and this result means that *Ruminococcus* faecis has a therapeutic effect for NAFLD in an independent manner of insulin, and means that it may be effectively used for treatment of nonalcoholic fatty liver disease patients with type 2 diabetes.

In particular, in order to confirm the treatment response sensitivity according to the difference in insulin resistance, the db/db model and the CDAHFD model as a comparative model were selected. As nonalcoholic fatty liver disease is induced without insulin resistance in case of the CDAHFD model, it is suitable for comparing the therapeutic effect according to insulin resistance, compared to the db/db model in which insulin resistance is induced. In case of the MCD model, it was not suitable for use as a control to confirm the sensitivity of the treatment response according to the difference in insulin resistance, as it causes a decrease in body functions including rapid body weight loss.

As shown in FIG. 3b, according to administration of *Ruminococcus* faecis, the ALT level was reduced by about 42.98%, and as shown in FIG. 3c, the AST level was reduced by about 41.00%, and as shown in FIG. 3d, the liver weight ratio to body weight was reduced by about 9.43%. Considering that the ALT level reduction ratio was about 2.6 times or more compared to approximately 16.40% decrease in ALT level in the CDAHFD model of FIG. 2b, the AST level reduction ratio was about 2.2 times or more compared to approximately 18.18% decrease in AST level in the CDAHFD model of FIG. 2c, and the liver weight ratio to body weight was significantly reduced in the animal model having insulin resistance whereas the liver weight ratio to body weight was not significantly reduced in the CDAHFD model of FIG. 2d, *Ruminococcus* faecis has a difference in insulin resistance, or a difference in sensitivity related to improvement or treatment of liver injury according to the difference of the presence or absence of occurrence of type 2 diabetes, and shows a significantly excellent therapeutic effect in a type 2 diabetes subject.

Example 4: Fibrosis Therapeutic Effect of *Ruminococcus bromii*

(1) Significantly Reduced *Ruminococcus bromii* in Nonalcoholic Fatty Liver Disease Group 171 subjects demonstrated as having NAFLD and 31 subjects not having NAFLD by biopsy were included, and NAFLD was classified histologically. DNA from fecal samples was extracted using QIAamp DNA Stool Mini Kit (Qiagen, Hilden, Germany). Sequencing targeting the V4 region of the 16S rRNA gene was performed using MiSeq system (Illumina, San Diego, CA, USA), and additional analysis of the sequencing data was performed using QIIME™ pipeline (v 1.8.0; http://qiime.org/). As shown in FIG. 4a, it was shown that *Ruminococcus bromii* was significantly reduced in the liver fibrosis disease group.

(2) Verification of Therapeutic Effect of Nonalcoholic Fatty Liver of *Ruminococcus Bromii*

Next, whether *Ruminococcus bromii* shown as significantly reduced in the nonalcoholic fatty liver disease group had a therapeutic effect for nonalcoholic fatty liver was confirmed.

Specifically, *Ruminococcus bromii* (ATCC no. 27255) was distributed from ATCC (American Type Culture Collection, Manassas, VA, USA) and cultured in modified PYG medium under an anaerobic condition, and collected after 24 hours, and washed using PBS (+0.5% cysteine) twice, and fed orally.

After 1-week environmental adaptation of C57BL/6N mice in the standard chow diet, streptomycin (1 g/L) was dissolved in drinking water and fed for 1 week for intestinal settlement of *Ruminococcus bromii*. For 5 weeks thereafter, mice were fed a methionine and choline deficient L-amino acid diet (MCD) (Research diet, New Brunswick, NJ, USA; Cat. no.: A02082002B) at the same time, and one of *Ruminococcus bromii* suspended so as to contain $10^9$ CFU in 200 μL PBS or control PBS (sham) was orally administered daily. After 5 weeks of administration, mice were euthanized and biochemical analysis, anatomical analysis, confirmation of expression of markers of liver fibrosis occurrence and proliferation, and bile acid analysis were performed.

However, as shown in FIG. 4b to FIG. 4c, a significant change was not shown in the liver ratio in the body weight and ALT level, when *Ruminococcus bromii* was administered (MCD+R. bromii), compared to the control-administered mice (MCD).

*Ruminococcus bromii* did not show a therapeutic effect for nonalcoholic fatty liver, and from this, not all the species shown as reduced in the nonalcoholic fatty liver disease group had a therapeutic effect for nonalcoholic fatty liver, and in particular, even if the species belongs to the same genus as *Ruminococcus* faecis, not all of them had a therapeutic effect for nonalcoholic fatty liver, and therefore, it could be seen that the nonalcoholic therapeutic effect is a unique effect of *Ruminococcus* faecis. In addition, although *Ruminococcus bromii* was significantly reduced in the nonalcoholic fatty liver disease group, it did not show any therapeutic effect for nonalcoholic fatty liver when administered, so it was difficult to predict that administration of the reduced strain in the nonalcoholic fatty liver would lead to alleviate the severity of the disease.

Example 5: Culture and Production of *Ruminococcus faecis*

(1) Optimal Medium Search

To search optimal medium for *Ruminococcus faecis* (accession number KCTC no. 5757), culturability was confirmed in the YBHI medium comprising Bacto™ brain heart infusion (BHI) Medium (BD, Franklin Lakes, NJ, USA) on the market, Difco™ Reinforced Clostridial Medium (RCM medium) (BD, Franklin Lakes, NJ, USA), MB cell BL broth (BL medium) (Kisan Bio, Seoul, Republic of Korea), Difco™ Lactobacilli MRS broth (MRS medium) (BD, Franklin Lakes, NJ, USA), MB cell Gifu anaerobic medium (GAM medium) (Kisan Bio, Seoul, Republic of Korea) on the market, and the FMK1028 medium prepared in the present invention. The culturability for optimal medium selection was evaluated based on the absorbance increase and pH decrease after culture, and cell homogeneity confirmed by a microscope speculum. The compositions of the YBHI medium and FMK1028 medium were shown in Table 2 and Table 3 below, respectively.

TABLE 2

| YBHI medium | |
|---|---|
| Components | g/L |
| Bacto ™ brain heart infusion | 37 |
| Yeast Extract | 5 |
| Cellobiose | 1 |
| Maltose | 1 |
| L-cysteine | 0.5 |

TABLE 3

| FMK1028 medium | |
|---|---|
| Components | g/L |
| Glucose | 10 |
| Yeast Extract | 45 |
| Soy peptone | 10 |
| Sodium acetate | 3 |
| Sodium chloride | 5 |
| L-cysteine | 0.5 |

In all the media used for optimal medium search were adjusted to pH 6.8 before sterilization. The pre-culture of *Ruminococcus faecis* cultured in YBHI medium for 14 hours was inoculated so that the final volume ratio was 1% in YBHI medium, RCM medium, BL medium, MRS medium, GAM medium, or FMK1028 medium, respectively. After inoculation, under an anaerobic condition at 37° C., standing culture was carried out, and after 14 hours, the absorbance at 600 nm and pH of the culture solution were measured and the cell morphology was observed. The absorbance was measured using Orion Aquamate 8000 spectrometer (Thermo Scientific, Waltham, MA, USA), and pH was measured with SevenCompact pH/Ion meter (Mettler Toledo, Columbus, OH, USA). The cell morphology was observed with Optinity KB-320 optical microscope (Korea Labtech, Gyeonggi-do, Republic of Korea).

FIG. 5a is the result of comparing the culture potential of *Ruminococcus faecis* and cell morphology. As shown in FIG. 5a, the absorbance of the culture solution after the culture for 14 hours was the highest in the FMK1028 medium, and then, it was high in the order of YBHI medium, GAM medium, MRS medium, BL medium, and RCM medium. The pH of the culture solution after culture was the lowest in FMK1028 medium, and then, it was low in the order of BL medium, YBHI medium, MRS medium, RCM medium, and GAM medium. The result of observation with a microscope, the cell homogeneity derived from FMK1028 and GAM medium was most excellent, and then, the cell cultured in YBHI medium was excellent.

Overall, culturability of *Ruminococcus faecis* was most excellent in FMK1028 medium prepared in the present invention.

(2) Optimal Medium Growth Curve and Viable Cell Count

The growth curve and viable cell count were measured using the FMK1028 medium with most excellent culture potential of *Ruminococcus faecis*. As a control group, YBHI medium was used.

The pre-culture solution of *Ruminococcus faecis* cultured in YBHI medium for 14 hours was inoculated so that the volume ratio was 1% in YBHI medium and FMK1028 medium, respectively. After inoculation, under an anaerobic condition, at 37° C., standing culture was progressed for 14 hours, and the absorbance at 600 nm of the culture solution was measured and shown by a growth curve.

For measuring the viable cell count, *Ruminococcus faecis* inoculated in each medium was cultured for 14 hours, and then diluted according to 10-fold serial dilution using GAM medium, and 0.1 mL of the diluted solution was collected and spread on a GAM medium agar plate, and then cultured under an anaerobic condition at 37° C. for 24 hours. After culture, the colonies on the agar plate in which about 30-300 colonies were formed were counted and converted into the viable cell count per unit volume of the culture solution (CFU/mL). The measured growth curve and viable cell count per unit volume were shown in FIG. 5b. As shown in FIG. 5b, *Ruminococcus faecis* reached a stationary phase after 8 hours of culturing in YBHI medium as the control group, showing the absorbance of 2.55. It showed a growth curve similar to YBHI until 8 hours after culture in FMK1028 medium, but continued to grow until 14 hours after culture, showing the absorbance of 6.18. As a result of measuring the viable cell count per unit volume after culture for 14 hours, 600 times higher viable cell count was confirmed in the YBHI medium than FMK1028 medium.

(3) Mass Culture and Pulverization Using Fermenter

The recovery time of cultured cells was confirmed by using a fermenter for mass culture and pulverization of *Ruminococcus faecis*. After inoculating 16 mL of the pre-cultured solution of *Ruminococcus faecis* in 8 L of FMK1028 medium, a fermenter (Fermentec, Chungcheongbuk-do, Republic of Korea) was operated and cultured under the anaerobic conditions of 37° C., 250 rpm. The growth curve and viable cell count according to the culture time were measured and shown in FIG. 5c. FIG. 5c is the result showing the growth curve and viable cell count of *Ruminococcus faecis* cultured by operating the fermenter.

As shown in FIG. 5c, *Ruminococcus faecis* reached a stationary phase after culture for 8 hours and showed the absorbance of 8.25 and the viable cell count of $5.15 \times 10^9$ CFU/mL. In 11 hours after culture in the stationary phase, the absorbance was reduced to 7.25 and the viable cell count was slightly decreased and shown as $4.95 \times 10^9$ CFU/mL. Unlike the result of stationary culture presented in FIG. 5b, it could be confirmed that the time to reach the stationary phase was shortened to 8 hours as a result of culturing using a fermenter, and the absorbance (6.18→8.25) and viable cell count ($1.2 \times 10^9$ CFU/mL→$5.15 \times 10^9$ CFU/mL) measurement results in the stationary phase were also improved compared with the result of culturing for 14 hours in flask batch culture.

Based on the above result, *Ruminococcus faecis* was mass-cultured using a fermenter. At 8 hours after culture, cells cultured under a condition of 7,000 rpm, 40 minutes were recovered using a 2236R high-speed centrifuge (Labogene, Lillerød, Denmark). The recovered cells were placed in a 300 mL beaker and mixed with a freeze-drying protective agent in a weight ratio of 1:1 using a magnetic bar and a stirrer for 20 minutes. The composition of the used freeze-drying protective agent was shown in Table 4 below. The cells mixed with the freeze-drying protective agent were frozen in a −80° C. ultra-low temperature freezer for 24 hours, freeze-dried for 72 hours, then finely pulverized and powdered.

TABLE 4

| Cryoprotective agents (CPA) | |
|---|---|
| Components | g/L |
| Sucrose | 200 |
| Potassium phosphate dibasic | 6 |
| Potassium phosphate monobasic | 4.5 |
| L-arginine | 4 |
| NaCl | 0.8 |

Finally, the viable cell count measured in the mass culture and pulverization process using a fermenter was shown in Table 5 below.

TABLE 5

| Culture condition | Culture container | 14 L jar vessel |
| --- | --- | --- |
| | Medium | FMK1028 |
| | Culture volume (L) | 8 |
| | Culture time (h) | 8 |

TABLE 5-continued

| Viable cells | Harvested cells (CFU/mL) | $5.50 \times 10^9 \pm 2.83 \times 10^8$ |
| --- | --- | --- |
| | Mixture with CPA (CFU/mL) | $1.43 \times 10^{11} \pm 2.41 \times 10^{10}$ |
| | Powder (CFU/g) | $2.67 \times 10^{10} \pm 5.28 \times 10^9$ |

The invention claimed is:

1. A method for alleviating or treating nonalcoholic fatty liver disease, comprising administering a pharmaceutical or food composition comprising a *Ruminococcus faecis* strain with accession number KCTC No. 5757 to a subject.

2. The method according to claim 1, wherein the subject has one or more characteristics of the following (1) to (5):
   (1) increased blood ALT concentration,
   (2) increased blood AST concentration,
   (3) reduced secondary bile acid concentration in cecum,
   (4) increased fibrotic gene expression, and
   (5) increased ratio of liver weight to body weight.

3. The method according to claim 1, wherein the nonalcoholic fatty liver is diabetic nonalcoholic fatty liver disease.

4. The method according to claim 1, wherein the composition is characterized by one or more characteristics of the following (1) to (5):
   (1) reducing blood ALT concentration,
   (2) reducing blood AST concentration,
   (3) increasing secondary bile acid concentration in cecum,
   (4) reducing fibrotic gene expression, and
   (5) reducing ratio of liver weight to body weight.

5. The method according to claim 4, wherein the secondary bile acid is one or more selected from the group consisting of deoxycholic acid (DCA), lithocholic acid (LCA), and ursodeoxycholic acid (UDCA).

6. The method according to claim 4, wherein the fibrotic gene is one or more selected from the group consisting of Col1a1, Timp1, and α-SMA.

7. The method according to claim 1, wherein the composition alleviates or treats nonalcoholic fatty liver disease independently of insulin.

8. The method according to claim 1, wherein the subject has insulin resistance or type 2 diabetes.

9. The method according to claim 1, wherein the subject has insulin resistance and is characterized by one or more of the following (1) to (3):
   (1) higher reduction ratio of blood ALT level compared to a control group having no insulin resistance,
   (2) higher reduction ratio of blood AST level compared to a control group having no insulin resistance,
   (3) higher reduction ratio of a ratio of liver weight to body weight compared to a control group having no insulin resistance.

10. The method according to claim 1, wherein a fibrosis marker gene is overexpressed in the subject.

11. The method according to claim 10, wherein the fibrosis marker gene is one or more selected from the group consisting of Col1a1, Timp1, and α-SMA.

12. The method according to claim 1, wherein the strain continues to grow after 8 hours of culturing in a culture medium including 5 to 30% (w/V) of carbon source concentration, 50 to 90% (w/v) of nitrogen source concentration, 5 to 15% (w/v) of mineral concentration, and 0.1 to 10% (w/v) of amino acid concentration.

13. The method according to claim 1, wherein the composition further comprises a freeze-drying protective agent.

14. The method according to claim 13, wherein the freeze-drying protective agent comprises one or more selected from the group consisting of sucrose, calcium phosphate, arginine, sodium chloride, fructose, potassium phosphate monobasic, potassium phosphate dibasic, and trehalose.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: (Synthetic) Cyclophilin A primer FWD

<400> SEQUENCE: 1
tggagagcac caagacagac a                                              21

<210> SEQ ID NO 2
<211> LENGTH: 19
<212> TYPE: DNA
<213> ORGANISM: Artificial Sequence
<220> FEATURE:
<223> OTHER INFORMATION: (Synthetic) Cyclophilin A primer RVS

<400> SEQUENCE: 2
tgccggagtc gacaatgat                                                 19

<210> SEQ ID NO 3
<211> LENGTH: 20
<212> TYPE: DNA
<213> ORGANISM: Artificial Sequence
<220> FEATURE:
<223> OTHER INFORMATION: (Synthetic) Col1a1 primer FWD

<400> SEQUENCE: 3
acctgtgtgt tccctactca                                                20

<210> SEQ ID NO 4
<211> LENGTH: 20
<212> TYPE: DNA
<213> ORGANISM: Artificial Sequence
<220> FEATURE:
<223> OTHER INFORMATION: (Synthetic) Col1a1 primer RVS

<400> SEQUENCE: 4
gactgttgcc ttcgcctctg                                                20

<210> SEQ ID NO 5
<211> LENGTH: 20
<212> TYPE: DNA
<213> ORGANISM: Artificial Sequence
<220> FEATURE:
<223> OTHER INFORMATION: (Synthetic) Timp1 primer FWD

<400> SEQUENCE: 5
tgcctgctgc gattacaacc                                                20

<210> SEQ ID NO 6
<211> LENGTH: 22
<212> TYPE: DNA
<213> ORGANISM: Artificial Sequence
<220> FEATURE:
<223> OTHER INFORMATION: (Synthetic) Timp1 primer RVS

```
<400> SEQUENCE: 6
ggaatggtgt ggtgatgcat gg                                              22

<210> SEQ ID NO 7
<211> LENGTH: 19
<212> TYPE: DNA
<213> ORGANISM: Artificial Sequence
<220> FEATURE:
<223> OTHER INFORMATION: (Synthetic) a-SMA primer FWD

<400> SEQUENCE: 7
ggctctgggc tctgtaagg                                                  19

<210> SEQ ID NO 8
<211> LENGTH: 20
<212> TYPE: DNA
<213> ORGANISM: Artificial Sequence
<220> FEATURE:
<223> OTHER INFORMATION: (Synthetic) a-SMA primer RVS

<400> SEQUENCE: 8
ctcttgctct gggcttcatc                                                 20
```